(12) United States Patent
Kim et al.

(10) Patent No.: US 7,723,520 B2
(45) Date of Patent: May 25, 2010

(54) RED ELECTROLUMINESCENT COMPOUNDS AND ORGANIC ELECTROLUMINESCENT DEVICE USING THE SAME

(75) Inventors: Hyun Kim, Seoul (KR); Young Jun Cho, Seoul (KR); Hyuck Joo Kwon, Seoul (KR); Bong Ok Kim, Seoul (KR); Sung Min Kim, Seoul (KR); Seung Soo Yoon, Seoul (KR)

(73) Assignee: SKC Haas Display Films Co., Ltd., Choongchungnamdo (KR)

( * ) Notice: Subject to any disclaimer, the term of this patent is extended or adjusted under 35 U.S.C. 154(b) by 0 days.

(21) Appl. No.: 12/220,367

(22) Filed: Jul. 24, 2008

(65) Prior Publication Data

US 2009/0062542 A1  Mar. 5, 2009

(30) Foreign Application Priority Data

Jul. 24, 2007  (KR) .................. 10-2007-0073804

(51) Int. Cl.
*C07F 15/00* (2006.01)
*B32B 15/00* (2006.01)

(52) U.S. Cl. .................. 546/2; 428/690; 428/917; 546/4; 546/10

(58) Field of Classification Search ............ 546/2, 546/4, 10; 428/690, 917
See application file for complete search history.

(56) References Cited

U.S. PATENT DOCUMENTS

| | | | |
|---|---|---|---|
| 5,779,937 A | 7/1998 | Sano et al. | |
| 5,858,560 A | 1/1999 | Nakamura et al. | |
| 5,922,480 A | 7/1999 | Nakamura et al. | |
| 6,083,634 A | 7/2000 | Shi | |
| 6,645,645 B1 | 11/2003 | Adachi et al. | |
| 6,936,716 B1 | 8/2005 | Lin | |
| 6,998,492 B2 | 2/2006 | Seo et al. | |
| 7,193,088 B2 | 3/2007 | Cheng et al. | |

FOREIGN PATENT DOCUMENTS

| | | |
|---|---|---|
| EP | 0 579 151 B1 | 10/1996 |
| EP | 0 652 273 B1 | 2/1998 |
| EP | 1 640 365 | 3/2006 |
| EP | 1 323 808 B1 | 10/2006 |
| JP | 2003-192691 | 7/2003 |
| JP | 2003-252888 | 9/2003 |
| JP | 2005 350415 | 12/2005 |
| WO | WO 98/37736 | 8/1998 |
| WO | WO 2006/059758 | 6/2006 |
| WO | WO 2006/098460 | 9/2006 |

OTHER PUBLICATIONS

European Search Report of corresponding European Application No. EP 08 16 1026, Mar. 13, 2009.
Seo et al.; "Highly efficient white organic light-emitting diodes using two emitting materials for three primary colors (red, green, and blue)"; Applied Physics Letters, AIP, American Institute of Physics; vol. 90, No. 20; May 16, 2007; pp. 203507-1,-2 and -3.
Seo et al.; "P-164: Highly Efficient White Organic Light-Emitting Diodes Using Two Emitting Materials for Three Primary Colors (Red, Green and Blue)" SID 2007, 2007 SID International Symposium, Society for Information Display; vol. XXXVIII; May 20, 2007; pp. 813-817.
Agarwal et al.: "Synthesis, characterization, photophysical and electrochemical properties of new phosphorescent dopants for OLEDs"; Tetrahedron Letters, Elsevier, Amsterdam, vol. 49, No. 17; Mar. 4, 2008; pp. 2710-2713.

*Primary Examiner*—Charanjit S Aulakh
(74) *Attorney, Agent, or Firm*—Edwin Oh

(57) ABSTRACT

The present invention relates to novel red phosphorescent compounds exhibiting high luminous efficiency, and organic electroluminescent devices comprising the same.

8 Claims, 3 Drawing Sheets

RED ELECTROLUMINESCENT COMPOUNDS AND ORGANIC ELECTROLUMINESCENT DEVICE USING THE SAME

The present invention relates to novel red electroluminescent compounds exhibiting high luminous efficiency and organic electroluminescent devices using the same.

The most important factor to determine luminous efficiency in an OLED is the type of electroluminescent material. Though fluorescent materials have been widely used as an electroluminescent material up to the present, development of phosphorescent materials is one of the best methods to improve the luminous efficiency theoretically up to four (4) times, in view of electroluminescent mechanism.

Up to now, iridium (III) complexes are widely known as phosphorescent material, including $(acac)Ir(btp)_2$, $Ir(ppy)_3$ and Firpic, as the red, green and blue one, respectively. In particular, a lot of phosphorescent materials have been recently investigated in Japan, Europe and America.

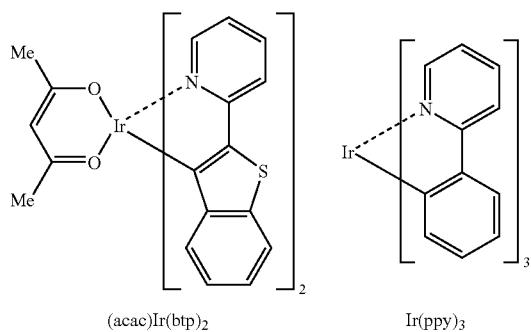

(acac)Ir(btp)$_2$    Ir(ppy)$_3$

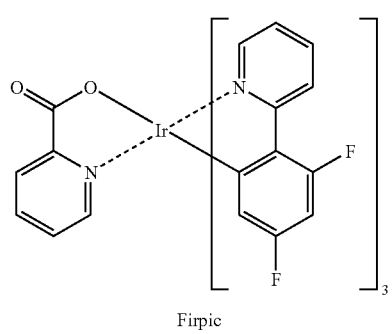

Firpic

Among conventional red phosphorescent materials, several materials are reported to have good EL properties. However, very rare materials among them have reached the level of commercialization. As the best material, an iridium complex of 1-phenyl isoquinoline may be mentioned, which is known to have excellent EL property and to exhibit color purity of dark red with high luminous efficiency. See A. Tsuboyama et al., *J. Am. Chem. Soc.* 2003, 125(42), 12971-12979.

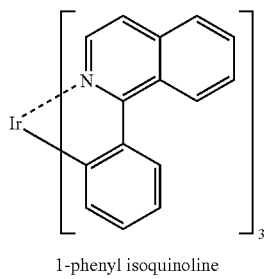

1-phenyl isoquinoline

Moreover, the red materials, having no significant problem of life time, have tendency of easy commercialization if they have good color purity or luminous efficiency. Thus, the above-mentioned iridium complex is a material having very high possibility of commercialization due to its excellent color purity and luminous efficiency.

However, the iridium complex is still construed only as a material which is applicable to small displays, while higher levels of EL properties than those of known materials are practically required for an OLED panel of medium to large size.

As a result of intensive efforts of the present inventors to overcome the problems of conventional techniques as described above, they have developed novel red phosphorescent compounds to realize an organic EL device having excellent luminous efficiency and surprisingly improved lifetime.

The object of the invention is to provide compounds having the skeleton to give more excellent electroluminescent properties as compared to those of conventional red phosphorescent materials. Another object of the invention is to provide novel phosphorescent compounds which are applicable to OLED panels of medium to large size.

Thus, the present invention relates novel red phosphorescent compounds and organic electroluminescent devices employing the same in an electroluminescent layer. Specifically, the red phosphorescent compounds according to the invention are represented by Chemical Formula 1:

Chemical Formula 1

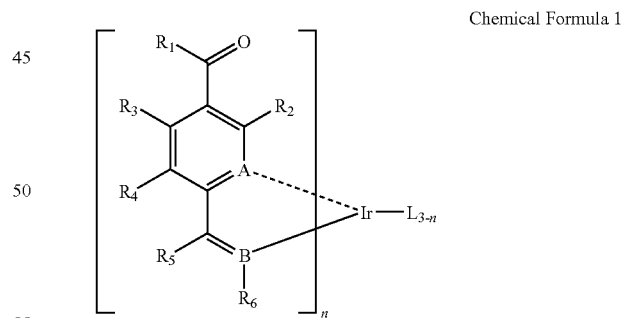

wherein, L is an organic ligand;
B is C (carbon) if A is N (nitrogen), and B is N if A is C;
$R_1$ represents a linear or branched $(C_1-C_{20})$alkyl or $(C_6-C_{20})$aryl;
$R_2$ through $R_4$ independently represent hydrogen, linear or branched $(C_1-C_{20})$alkyl, linear or branched $(C_1-C_{20})$alkoxy, $(C_3-C_{12})$cycloalkyl, $(C_6-C_{20})$aryl, halogen, tri$(C_1-C_{20})$alkylsilyl or tri$(C_6-C_{20})$arylsilyl;
$R_5$ and $R_6$ independently represent hydrogen, linear or branched $(C_1-C_{20})$alkyl, $(C_6-C_{20})$aryl or halogen; $R_5$ and $R_6$ may be linked via $(C_3-C_{12})$alkylene or $(C_3-C_{12})$alkenylene optionally with a fused ring to form an alicyclic ring, or a monocyclic or polycyclic aromatic ring; the alkyl or aryl of $R_5$ and $R_6$, or the alicyclic ring, or the monocyclic or polycyclic aromatic ring formed therefrom by linkage via $(C_3-C_{12})$alkylene or $(C_3-C_{12})$alkenylene optionally containing a fused ring may be further substituted by one or more substituent(s) selected from linear or branched $(C_1-C_{20})$alkyl optionally substituted with halogen, $(C_1-C_{20})$alkoxy, halogen, tri$(C_1-C_{20})$alkylsilyl, tri$(C_6-C_{20})$arylsilyl and $(C_6-C_{20})$aryl;

the alkyl, alkoxy, cycloalkyl and aryl of $R_1$ through $R_4$ may be further substituted by one or more substituent(s) selected from linear or branched $(C_1-C_{20})$alkyl optionally substituted with halogen, $(C_1-C_{20})$alkoxy, halogen, tri$(C_1-C_{20})$alkylsilyl, tri$(C_6-C_{20})$arylsilyl and $(C_6-C_{20})$aryl; and n is an integer from 1 to 3.

The alicyclic ring, or the monocyclic or polycyclic aromatic ring formed from $R_5$ and $R_6$ of the compound of Chemical Formula 1 according to the present invention by linkage via $(C_3-C_{12})$alkylene or $(C_3-C_{12})$alkenylene optionally containing a fused ring may be benzene, naphthalene, anthracene, fluorene, indene, phenanthrene or pyridine. In Chemical Formula 1, the species enclosed by square brackets ([ ]) act as primary ligands of iridium, and L as subsidiary ligands. The phosphorescent compounds according to the present invention include the complexes with a ratio of primary ligand:subsidiary ligand=2:1 (n=2), in addition to the tris-chelated complexes without subsidiary ligand (L) (n=3).

The organic phosphorescent compounds represented by Chemical Formula 1 according to the present invention may be exemplified by the compounds represented by Chemical Formulas 2 to 7:

Chemical Formula 2

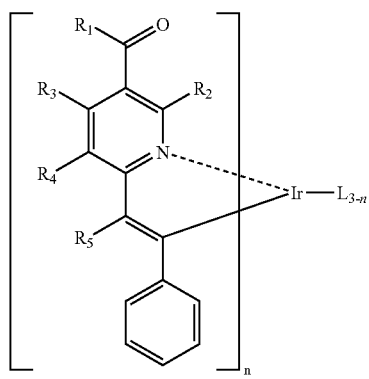

Chemical Formula 3

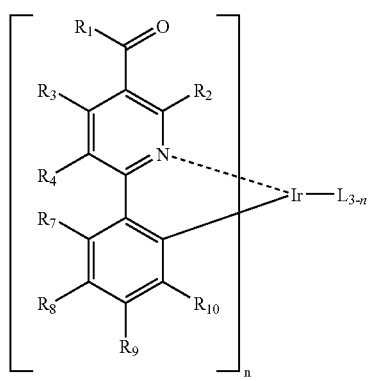

Chemical Formula 4

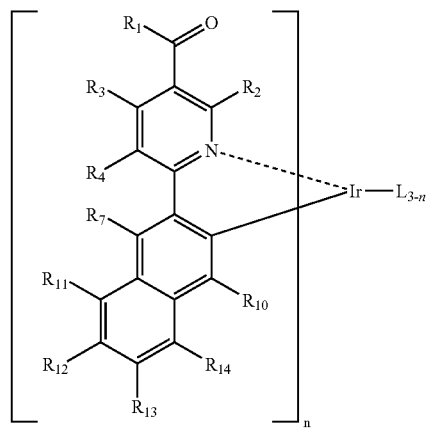

Chemical Formula 5

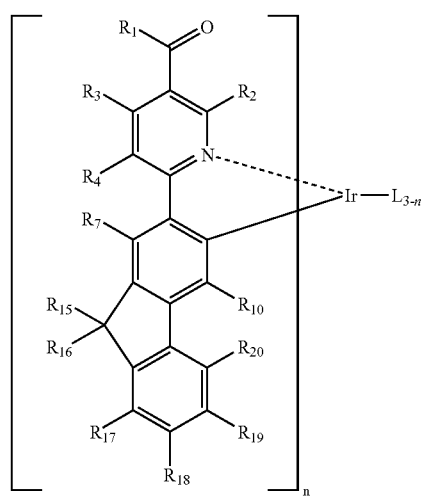

Chemical Formula 6

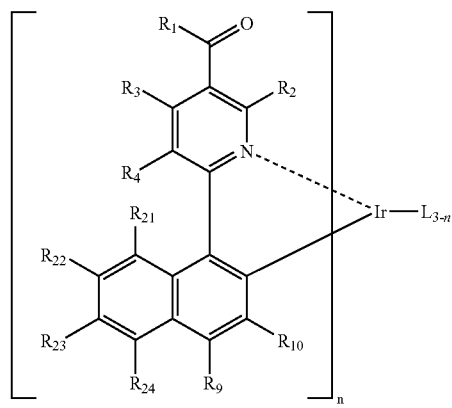

-continued

Chemical Formula 7

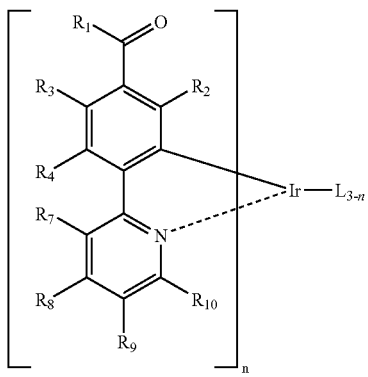

wherein, L, $R_1$, $R_2$, $R_3$, $R_4$, $R_5$ and n are defined as in Chemical Formula 1;

$R_7$ through $R_{14}$ and $R_{17}$ through $R_{24}$ independently represent hydrogen, linear or branched ($C_1$-$C_{20}$)alkyl optionally substituted with halogen, ($C_1$-$C_{20}$)alkoxy, halogen, tri($C_1$-$C_{20}$)alkylsilyl, tri($C_6$-$C_{20}$)arylsilyl or ($C_6$-$C_{20}$)aryl; and $R_{15}$ and $R_{16}$ independently represent hydrogen or linear or branched ($C_1$-$C_{20}$)alkyl.

An embodiment of the present invention is characterized in that $R_1$ of Chemical Formulas 2 to 7 represents methyl, ethyl, n-propyl, i-propyl, n-butyl, t-butyl, phenyl, biphenyl, naphthyl, t-butylphenyl or fluorophenyl; $R_2$ through $R_5$ independently represent hydrogen, methyl, ethyl, n-propyl, i-propyl, n-butyl or t-butyl; $R_7$ through $R_{14}$ and $R_{17}$ through $R_{24}$ independently represent hydrogen, methyl, ethyl, n-propyl, i-propyl, n-butyl, t-butyl, fluoro, methoxy, ethoxy, butoxy, phenyl, biphenyl, trimethylsilyl, triphenylsilyl or trifluoromethyl; $R_{15}$ and $R_{16}$ independently represent hydrogen or methyl.

The organic phosphorescent compounds of Chemical Formula 1 according to the present invention may be specifically exemplified by, but are not limited to, the following compounds:

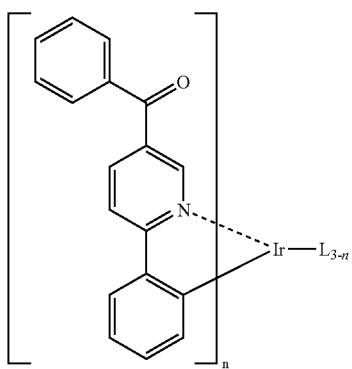

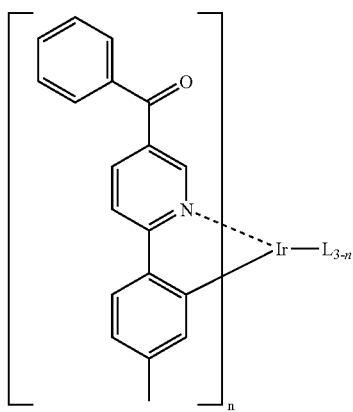

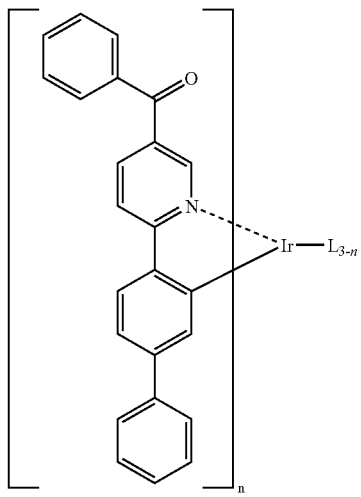

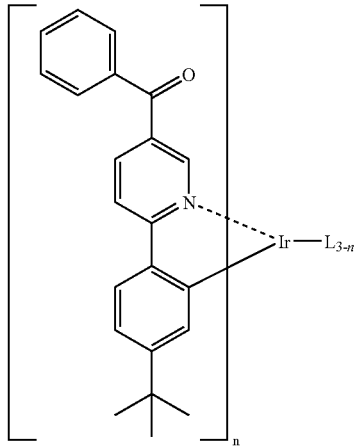

-continued
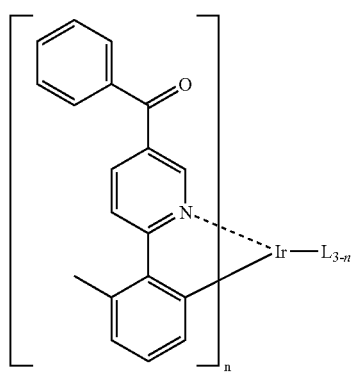
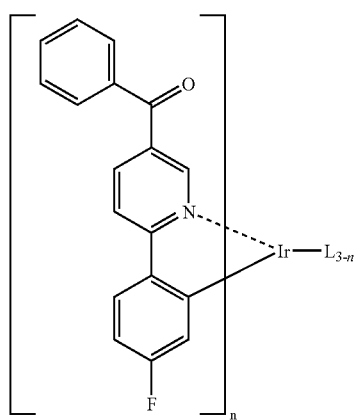
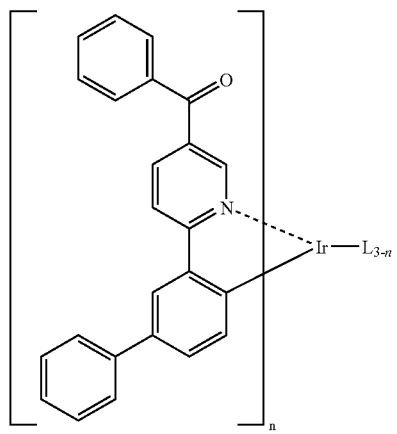
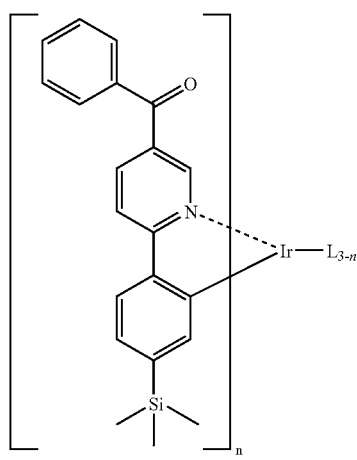
-continued
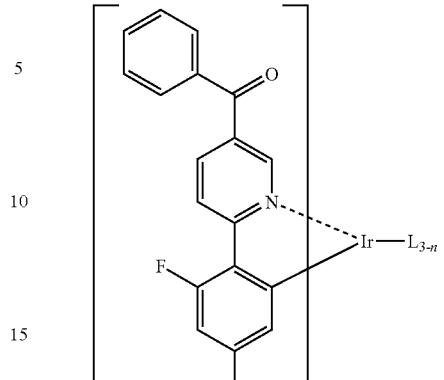
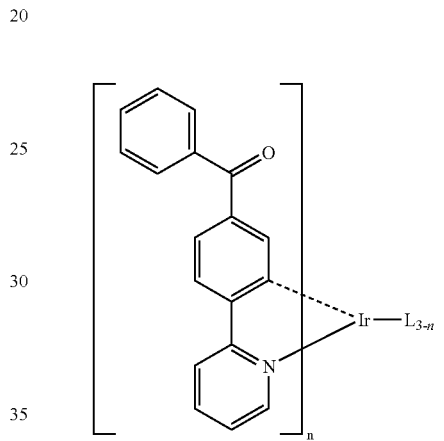
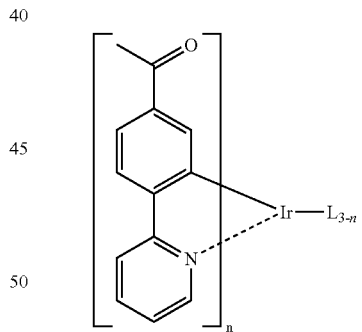
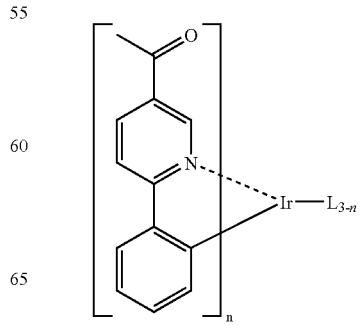

-continued
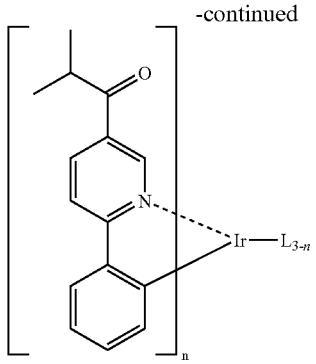
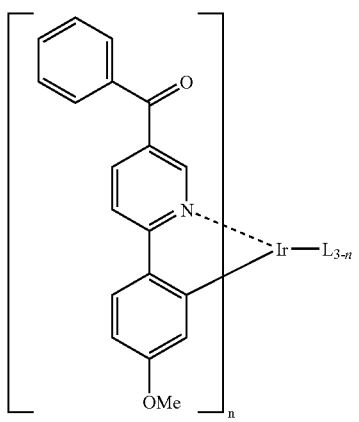
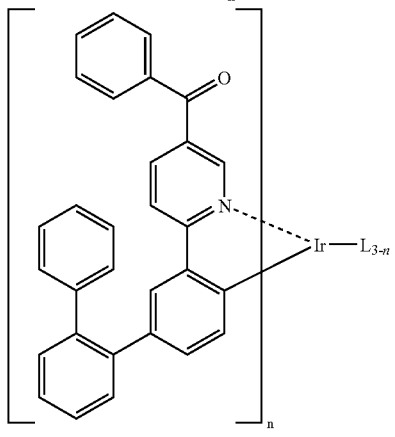
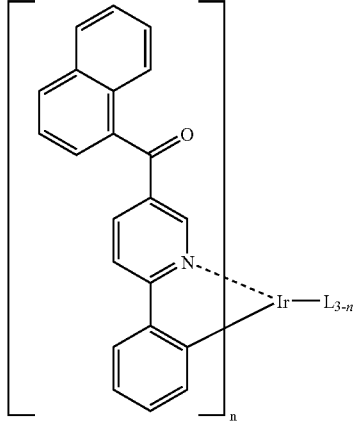
-continued
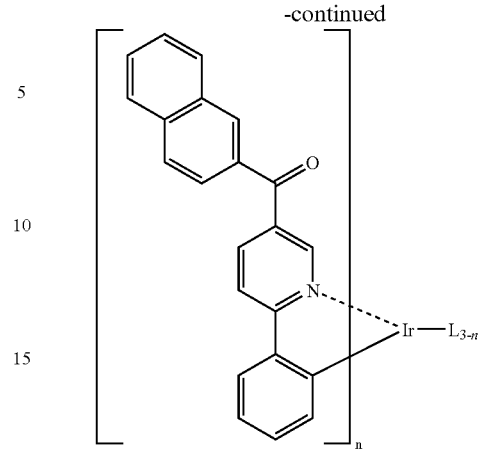
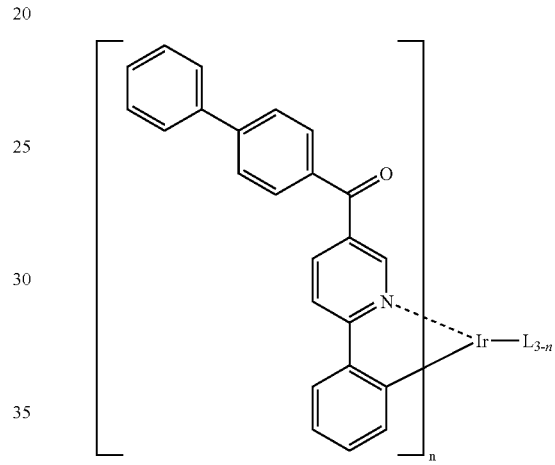
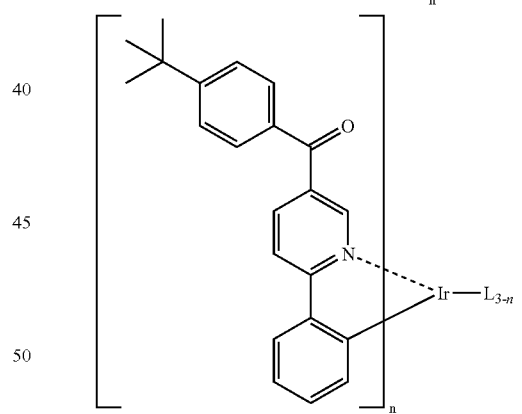
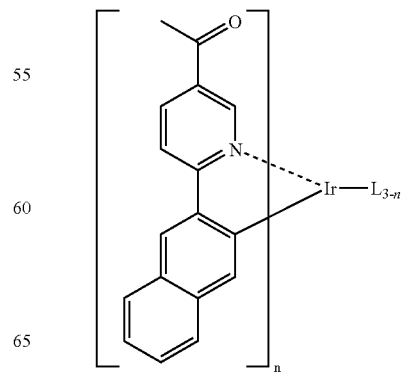

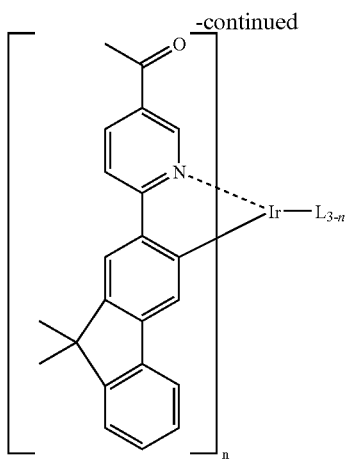
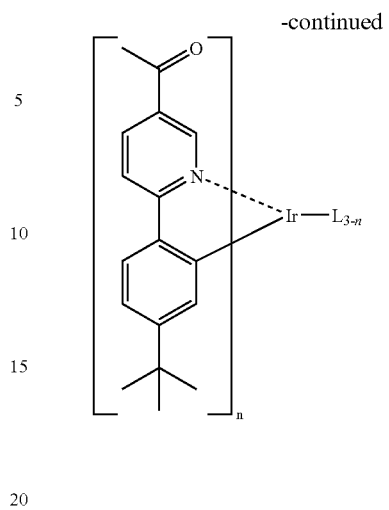
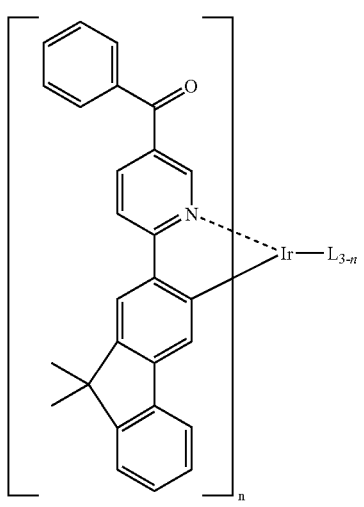
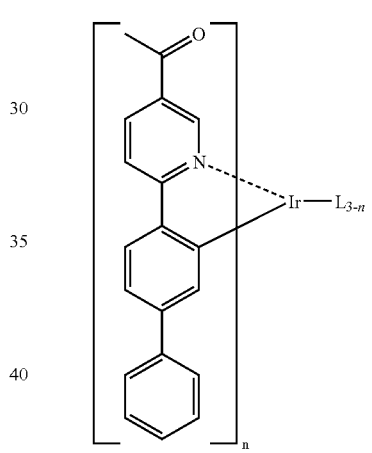
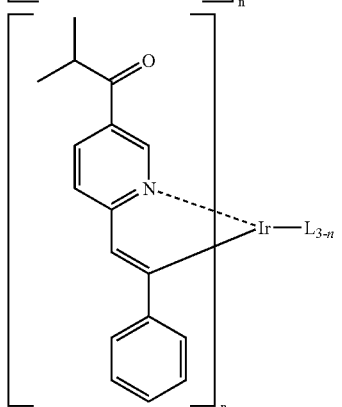
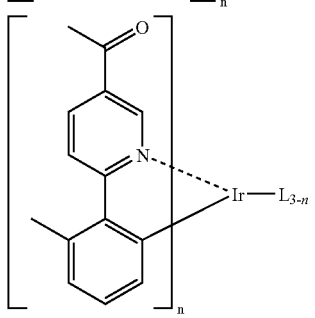
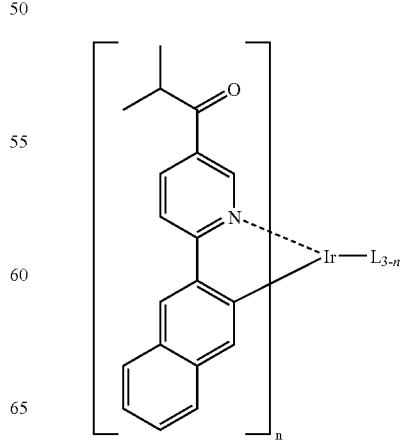

-continued
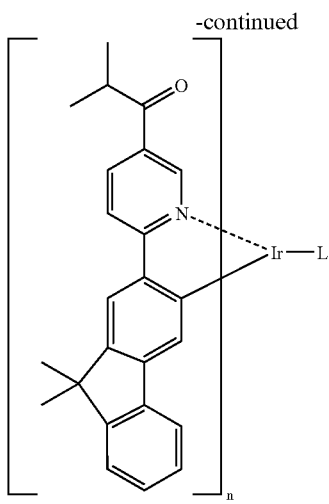
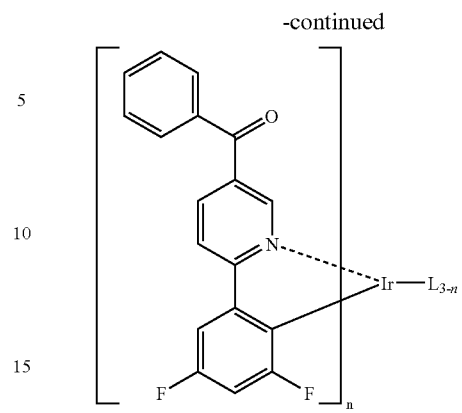
wherein, L is an organic ligand, and n is an integer from 1 to 3.
The subsidiary ligand L of Chemical Formula 1 according to the invention comprises one of the following structures:
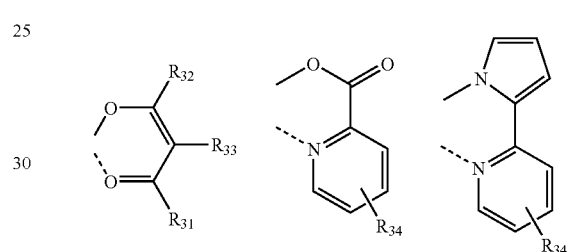
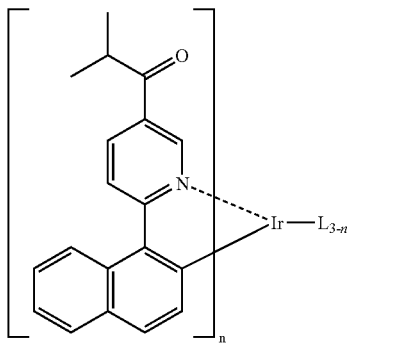
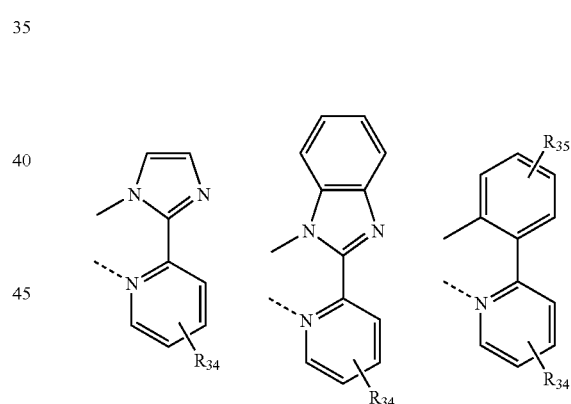
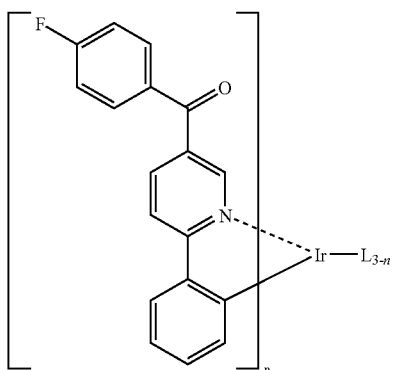
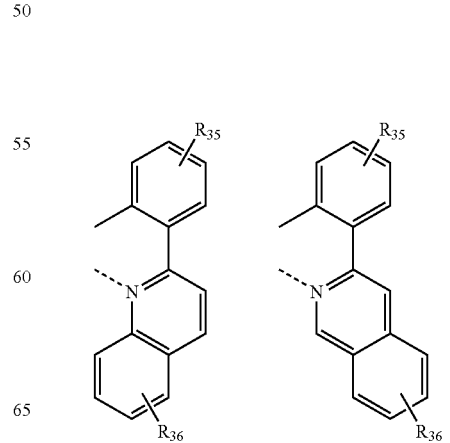
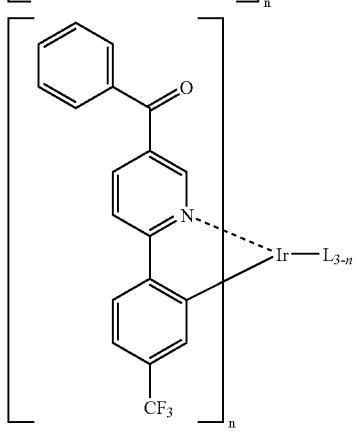

-continued

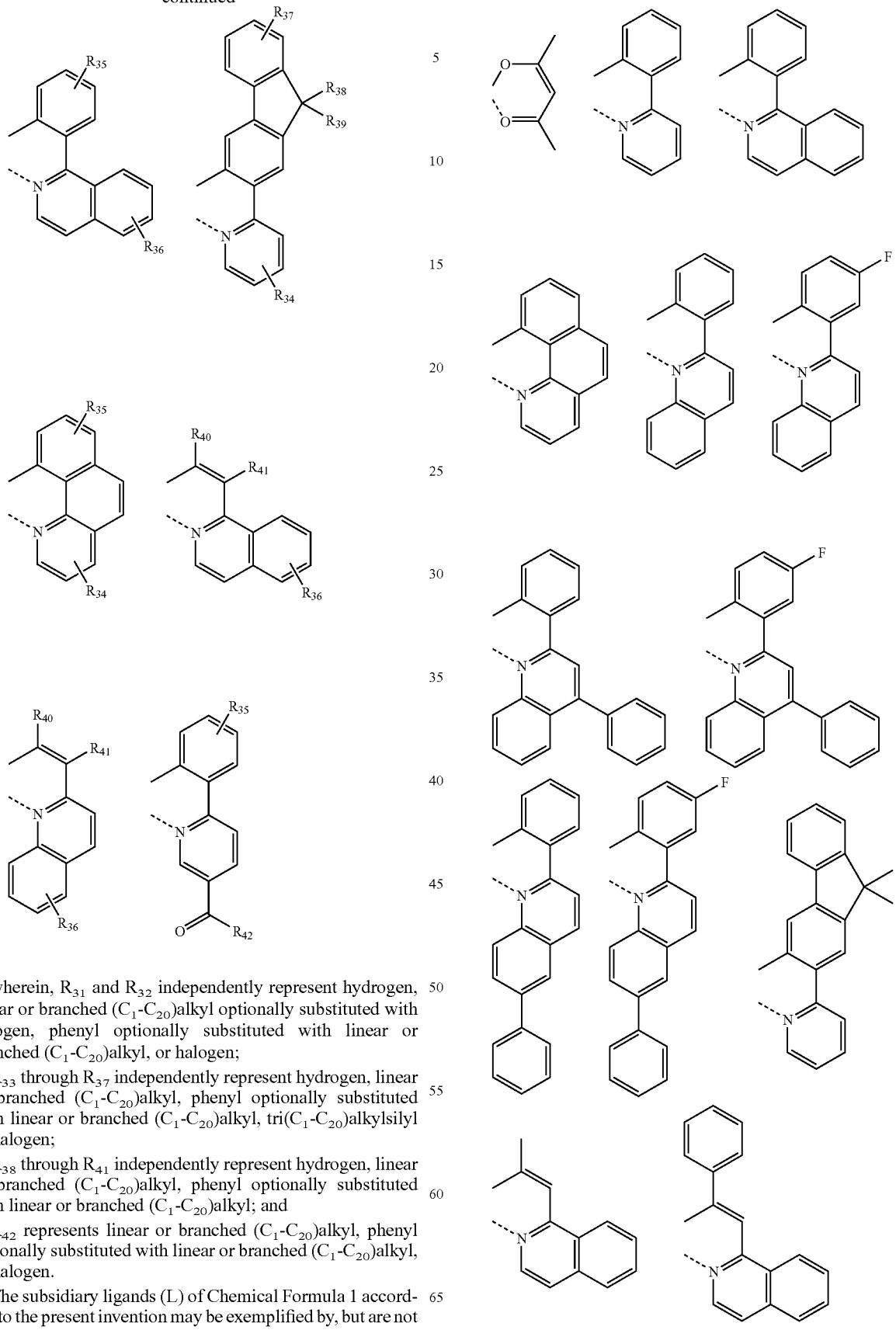

wherein, $R_{31}$ and $R_{32}$ independently represent hydrogen, linear or branched $(C_1\text{-}C_{20})$alkyl optionally substituted with halogen, phenyl optionally substituted with linear or branched $(C_1\text{-}C_{20})$alkyl, or halogen;

$R_{33}$ through $R_{37}$ independently represent hydrogen, linear or branched $(C_1\text{-}C_{20})$alkyl, phenyl optionally substituted with linear or branched $(C_1\text{-}C_{20})$alkyl, tri$(C_1\text{-}C_{20})$alkylsilyl or halogen;

$R_{38}$ through $R_{41}$ independently represent hydrogen, linear or branched $(C_1\text{-}C_{20})$alkyl, phenyl optionally substituted with linear or branched $(C_1\text{-}C_{20})$alkyl; and $R_{42}$ represents linear or branched $(C_1\text{-}C_{20})$alkyl, phenyl optionally substituted with linear or branched $(C_1\text{-}C_{20})$alkyl, or halogen.

The subsidiary ligands (L) of Chemical Formula 1 according to the present invention may be exemplified by, but are not limited to, the following structures.

-continued

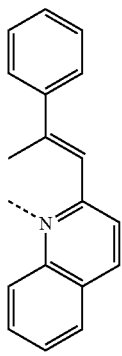

The process for preparing the organic phosphorescent compounds according to the present invention is described by referring to Reaction Schemes 1 to 3 shown below:

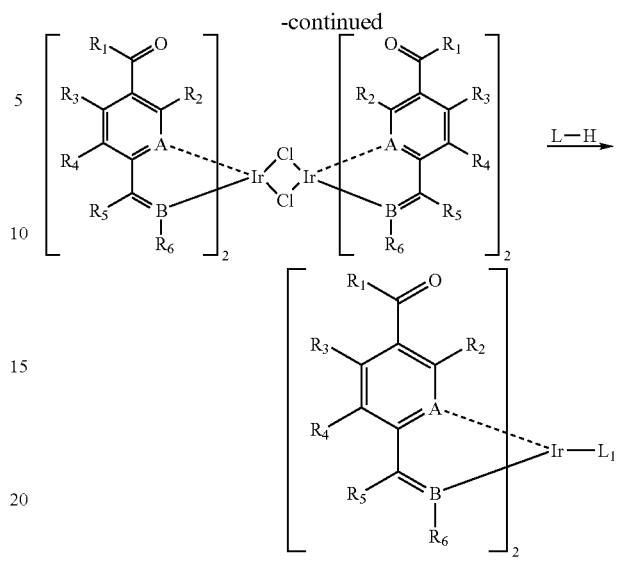

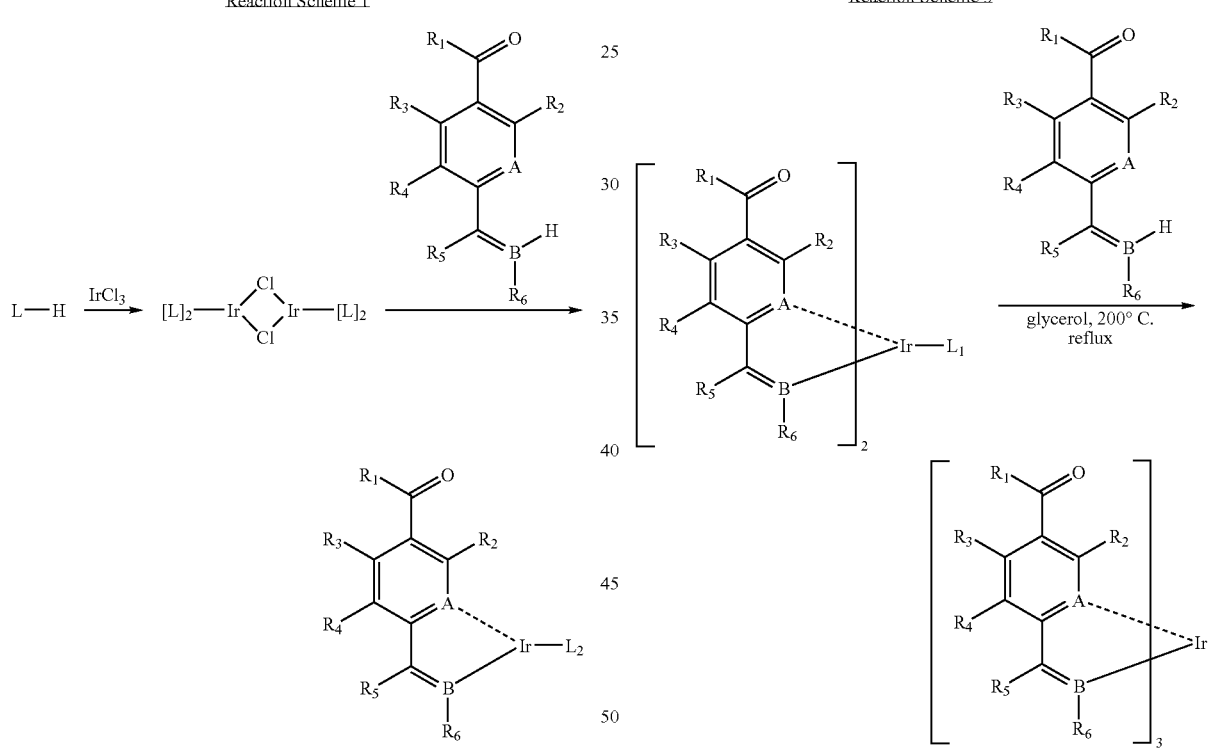

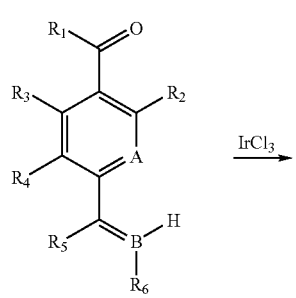

wherein, A, B, $R_1$ through $R_6$ and L are defined as in Chemical Formula 1.

Reaction Scheme 1 provides a compound of Chemical Formula 1 with n=1, in which iridium trichloride ($IrCl_3$) and a subsidiary ligand (L) compound are mixed in a solvent at a molar ratio of 1:2~3, and the mixture is heated under reflux to obtain isolated diiridium dimer. In the reaction stage, the preferable solvent is alcohol or a mixed solvent of alcohol/water, such as 2-ethoxyethanol, and 2-ethoxyethanol/water mixtures. The isolated diiridium dimer is then heated with a primary ligand compound in organic solvent to provide an organic phosphorescent iridium compound having the ratio of primary ligand:subsidiary ligand of 1:2 as the final product.

The reaction is carried out with AgCF$_3$SO$_3$, Na$_2$CO$_3$ or NaOH being admixed with organic solvent such as 2-ethoxyethanol and 2-methoxyethylether.

Reaction Scheme 2 provides a compound of Chemical Formula 1 with n=2, in which iridium trichloride (IrCl$_3$) and a primary ligand compound are mixed in a solvent at a molar ratio of 1:2~3, and the mixture is heated under reflux to obtain isolated diiridium dimer. In the reaction stage, the preferable solvent is alcohol or a mixed solvent of alcohol/water, such as 2-ethoxyethanol, and 2-ethoxyethanol/water mixture. The isolated diiridium dimer is then heated with a subsidiary ligand (L) compound in organic solvent to provide an organic phosphorescent iridium compound having the ratio of primary ligand:subsidiary ligand of 2:1 as the final product.

The molar ratio of the primary ligand and the subsidiary ligand in the final product is determined by appropriate molar ratio of the reactant depending on the composition. The reaction may be carried out with AgCF$_3$SO$_3$, Na$_2$CO$_3$ or NaOH being admixed with organic solvent such as 2-ethoxyethanol, 2-methoxyethylether and 1,2-dichloromethane.

Reaction Scheme 3 provides a compound of Chemical Formula 1 with n=3, in which iridium complex prepared according to Reaction Scheme 2 and a primary ligand compound are mixed in glycerol at a molar ratio of 1:2~3, and the mixture is heated under reflux to obtain organic phosphorescent iridium complex coordinated with three primary ligands.

The compounds employed as a primary ligand in the present invention can be prepared according to Reaction Scheme 4 or 5, on the basis of conventional processes.

Reaction Scheme 4

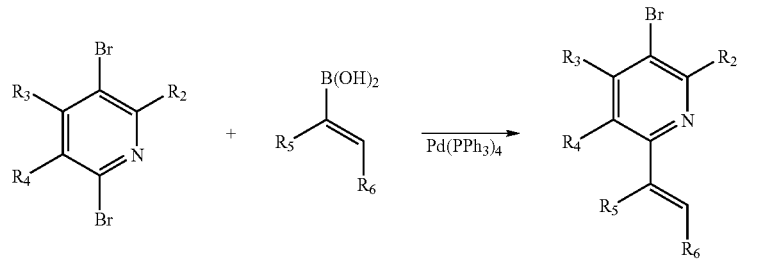

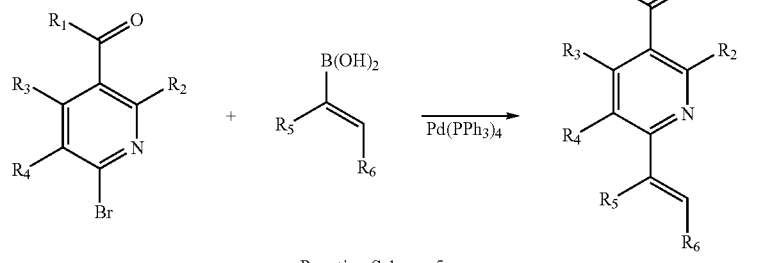

Reaction Scheme 5

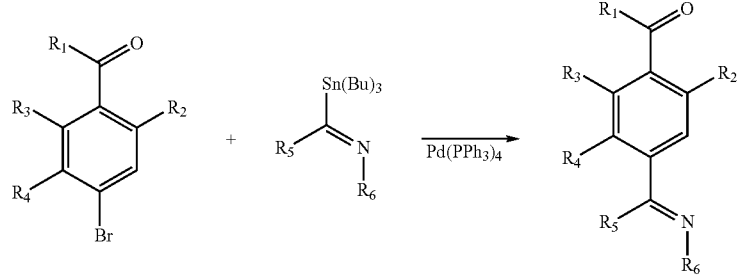

wherein, R$_1$ through R$_6$ are defined as in Chemical Formula 1.

Figure 1:
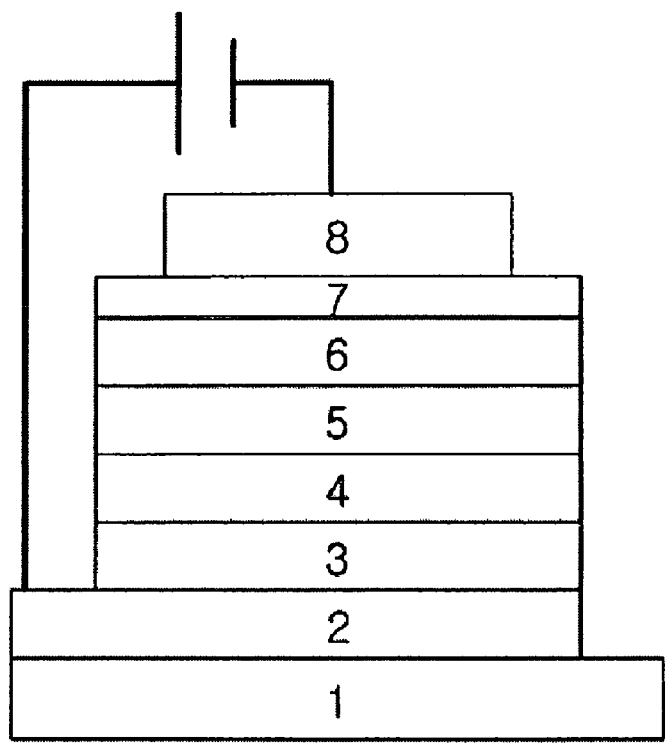
FIG. 1 is a cross-sectional view of an OLED.
Figure 2:
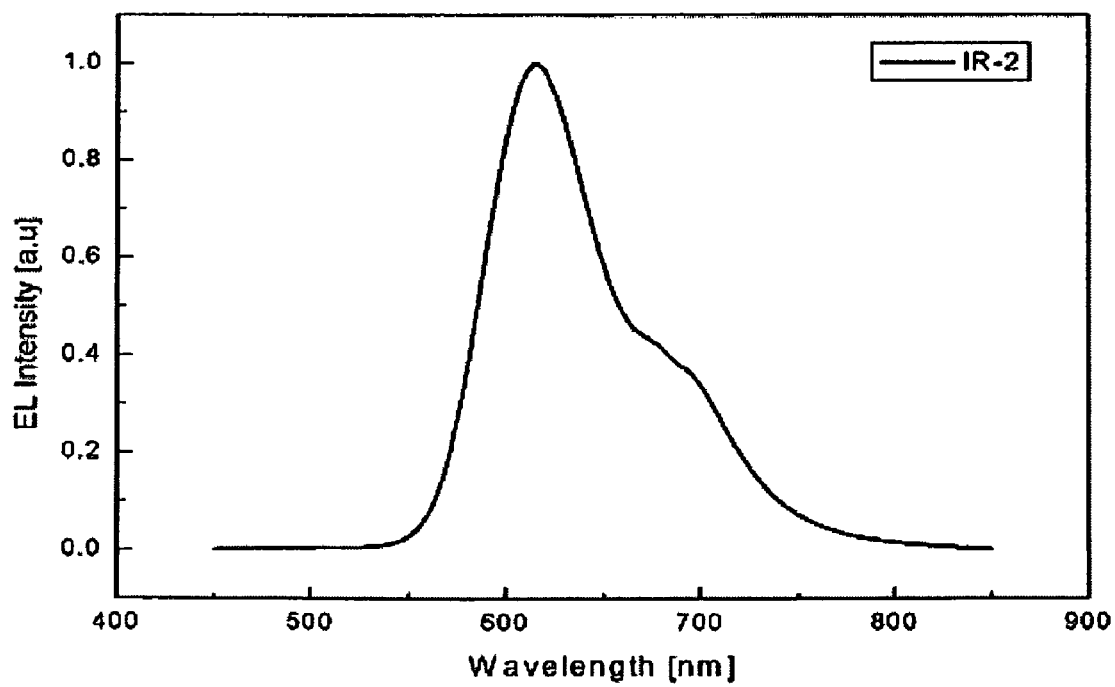
FIG. 2 is an EL spectrum of an OLED employing the red phosphorescent compound (102) according to the present invention as a dopant.
Figure 3:
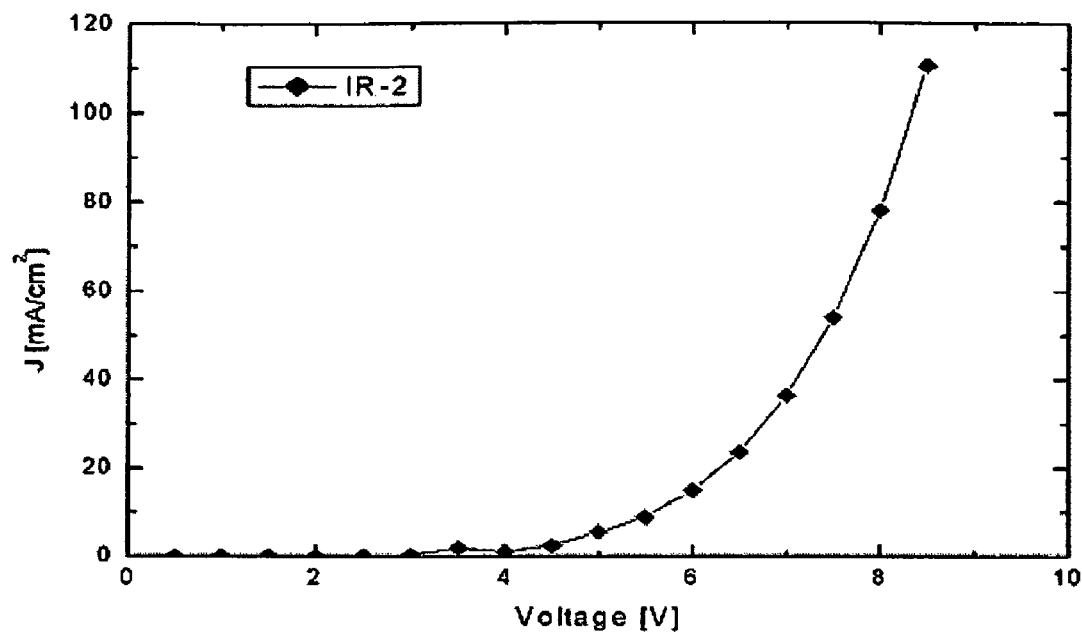
FIG. 3 shows current density-voltage property of an OLED employing the red phosphorescent compound (102) according to the present invention as a dopant.
Figure 4:
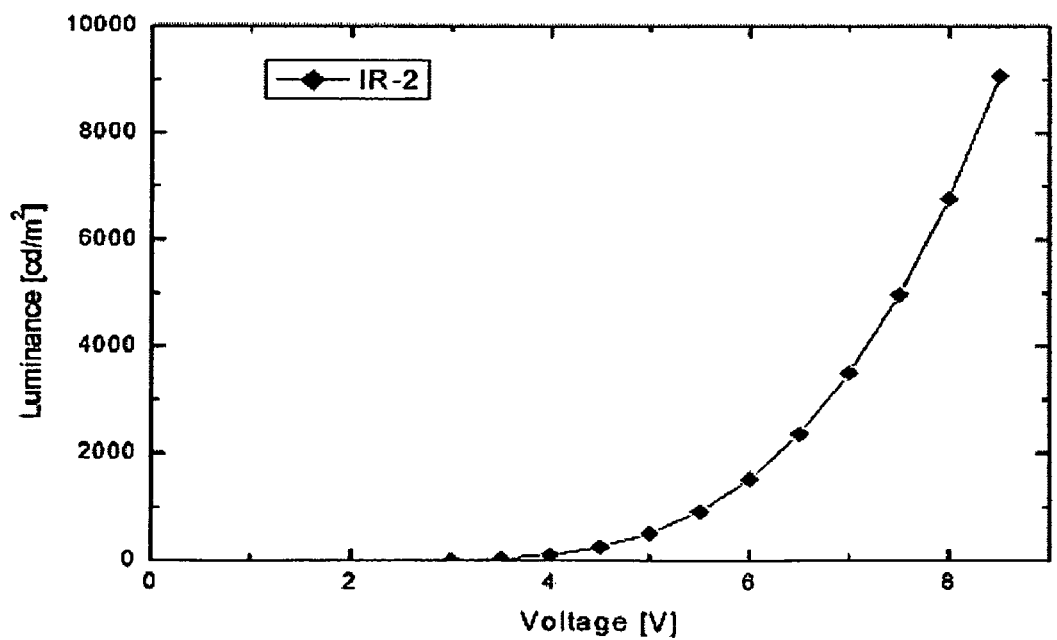
FIG. 4 shows luminance-voltage property of an OLED employing the red phosphorescent compound (102) according to the present invention as a dopant.
Figure 5:
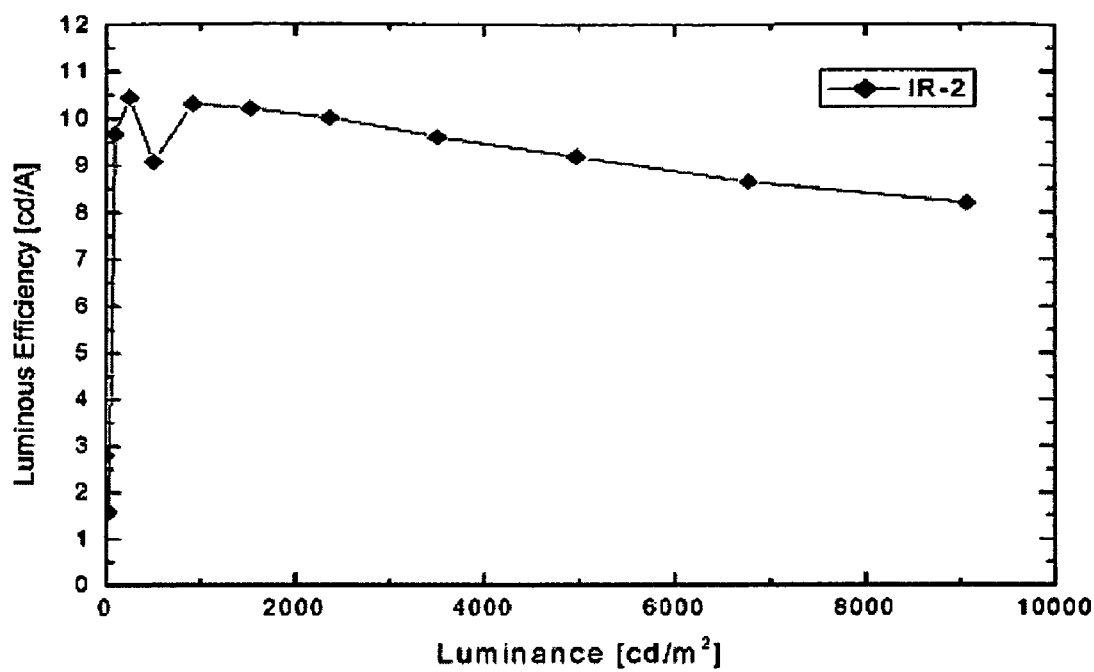
FIG. 5 shows luminous efficiency-luminance property of an OLED employing the red phosphorescent compound (102) according to the present invention as a dopant.

Description of symbols of significant parts of the drawings:
1: Glass
2: Transparent electrode
3: Hole injection layer
4: Hole transportation layer
5: Electroluminescent layer
6: Electron transportation layer
7: Electron injection layer
8: Al cathode The present invention is further described with respect to the processes for preparing novel organic phosphorescent compounds according to the invention by referring to the Examples, which are provided for illustration only but are not intended to limit the scope of the invention by any means.

PREPARATION EXAMPLE 1

Preparation of Compound (101)

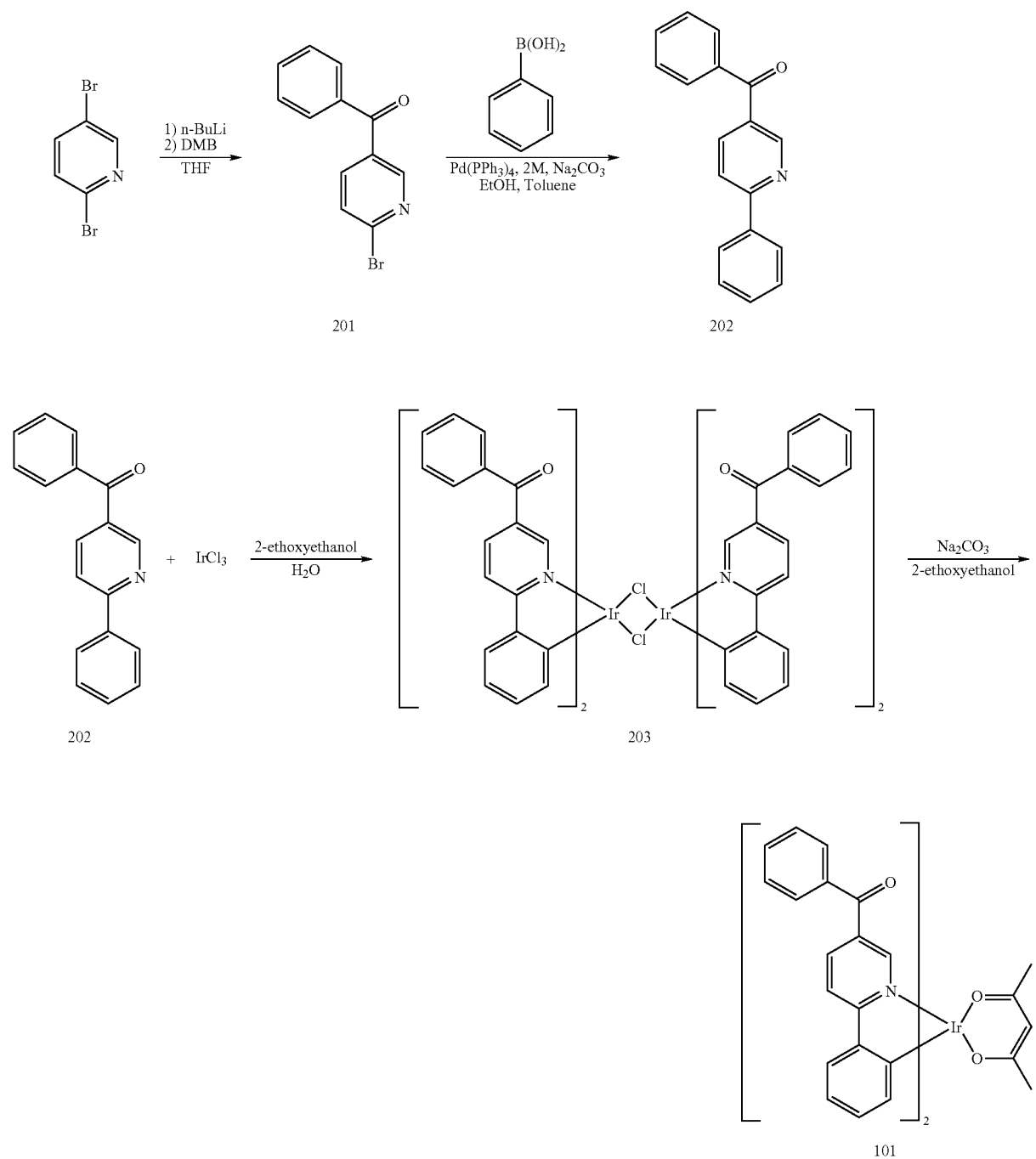

Preparation of Compound (201)

A 2000 mL round-bottomed flask was charged with 2,5-dibromopyridine (25.0 g, 105 mmol), which was then dissolved with diethyl ether (1240 mL) under argon atmosphere. Under the temperature condition of −75° C., n-BuLi (80 mL) (1.6 M in hexane, 127 mmol) was slowly added dropwise thereto. After stirring for 30 minutes, a solution of N,N-dimethylbenzamide (23.6 g, 158 mmol) dissolved in diethyl ether (200 mL) was slowly added, and the resultant mixture was stirred for 35 minutes. When the reaction was completed, aqueous $NH_4Cl$ solution was added to the reaction mixture. Extraction with diethyl ether and purification via silica gel column chromatography gave Compound (201) (18.0 g, 68.9 mmol, yield: 65.6%).

Preparation of Compound (202)

A 500 mL round-bottomed flask was charged with Compound (201) (18.0 g, 68.9 mmol), phenylboronic acid (9.24 g, 75.8 mmol), toluene (160 mL), ethanol (80 mL) and $Pd(PPh_3)_4$ (3.18 g, 2.76 mmol), and the mixture was stirred under argon atmosphere. After adding aqueous 2 M $Na_2CO_3$ solution (80 mL), the resultant mixture was heated under reflux with stirring for 4 hours. When the reaction was completed, distilled water was added. Extraction with ethyl acetate and purification via silica gel column chromatography gave Compound (202) (15.5 g, 59.6 mmol, yield 86.5%).

Preparation of Compound (203)

A 500 mL round-bottomed flask was charged with Compound (202) (15.5 g, 59.6 mmol), iridium chloride ($IrCl_3$) (8.09 g, 27.1 mmol), 2-ethoxyethanol (210 mL) and distilled water (70 mL), and the mixture was heated under reflux and argon atmosphere for 24 hours. When the reaction was completed, the reaction mixture was cooled to ambient temperature. The precipitate was filtered and completely dried to obtain Compound (203) (18.2 g, 24.4 mmol).

Preparation of Compound (101)

A 500 mL round-bottomed flask was charged with Compound (203) (18.2 g, 24.4 mmol), 2,4-pentanedione (3.67 g, 36.6 mmol), $Na_2CO_3$ (7.76 g, 73.2 mmol) and 2-ethoxyethanol (300 mL), and the mixture was heated for 4 hours. When the reaction was completed, the reaction mixture was cooled to room temperature. The solid precipitate was filtered and purified via silica gel column chromatography and recrystallization to obtain the title compound, iridium complex (101) (8.47 g, 10.5 mmol, yield: 38.6%) as red crystals.

mp. >350° C.

$^1$H NMR (300 MHz, $CDCl_3$): δ=8.89 (d, J=1.2 Hz, 2H), 8.30 (dd, J=1.8 Hz, 8.4 Hz, 2H), 7.98 (d, J=8.7 Hz, 2H), 7.83-7.80 (m, 4H) 7.65-7.58 (m, 4H) 7.53-7.48 (m, 4H), 6.86 (td, J=1.2 Hz, 7.5 Hz, 2H), 6.74 (td, J=1.5 Hz, 7.5 Hz, 2H), 6.30 (dd, J=1.2 Hz, 7.8 Hz, 2H), 5.29 (s, 1H), 1.55 (s, 6H).

HRMS (FAB) calcd for $C_{41}H_{31}IrN_2O_4$ 808.1913: found, 808.1910

PREPARATION EXAMPLE 2

Preparation of Compound (131)

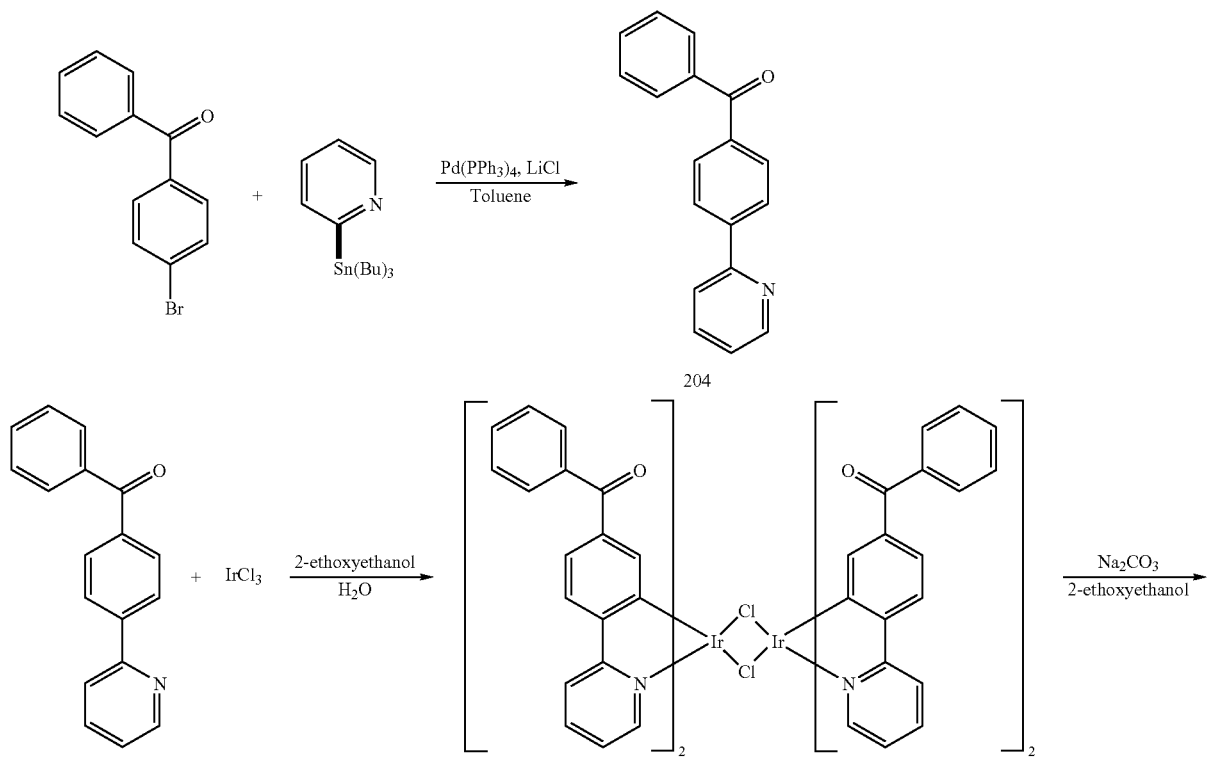

-continued

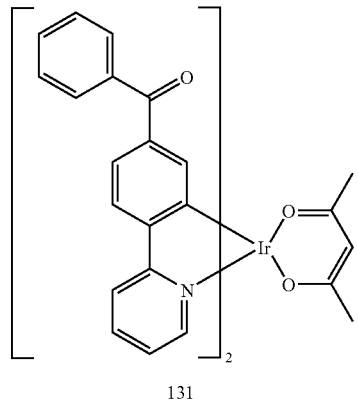
131

Preparation of Compound (204)

A 500 mL round-bottomed flask was charged with 4-bromobenzophenone (17.0 g, 65.2 mmol), Pd(PPh$_3$)$_4$ (3.14 g, 2.72 mmol) and LiCl (69.0 g, 163 mmol), and the mixture was stirred with toluene (250 mL) under argon atmosphere. After 5 minutes, a solution of tributyl(2-pyridyl)tin (20.0 g, 54.3 mmol) dissolved in toluene (20 mL) was added dropwise thereto. The mixture was stirred under reflux for 18 hours, and then cooled to room temperature. When the reaction was completed, aqueous KF solution was added to the reaction mixture. Extraction with ethyl acetate and purification via silica gel column chromatography gave Compound (204) (11.9 g, 45.9 mmol, yield: 84.5%).

Preparation of Compound (205)

A 500 mL round-bottomed flask was charged with Compound (204) (11.9 g, 45.9 mmol), iridium chloride (IrCl$_3$) (6.24 g, 20.9 mmol), 2-ethoxyethanol (210 mL) and distilled water (70 mL), and the mixture was heated under reflux and argon atmosphere for 24 hours. When the reaction was completed, the reaction mixture was cooled to ambient temperature. The precipitate was filtered and completely dried to obtain Compound (205) (10.6 g, 14.2 mmol).

Preparation of Compound (131)

A 500 mL round-bottomed flask was charged with Compound (205) (10.6 g, 14.2 mmol), 2,4-pentanedione (2.13 g, 21.3 mmol), Na$_2$CO$_3$ (4.52 g, 42.6 mmol) and 2-ethoxyethanol (300 mL), and the mixture was heated for 6 hours. When the reaction was completed, the reaction mixture was cooled to room temperature. The solid precipitate was filtered and purified via silica gel column chromatography. Recrystallization gave the title compound, iridium complex (131) (9.19 g, 11.4 mmol, yield: 54.4%) as red crystals.

mp. >350° C.

$^1$H NMR (300 MHz, CDCl$_3$): δ=8.51-8.49 (m, 2H), 7.86 (d, J=8.1 Hz, 2H), 7.68 (dd, J=1.5 Hz, 7.5 Hz, 2H), 7.63 (d, J=8.4 Hz, 2H), 7.57-7.54 (m, 4H), 7.49-7.44 (m, 2H), 7.34-7.28 (m, 6H), 7.16-7.11 (m, 2H), 6.59 (d, J=1.5 Hz, 2H), 5.25 (s, 1H), 1.80 (s, 6H)

HRMS (FAB) calcd for C$_{41}$H$_{31}$IrN$_2$O$_4$ 808.1913: found, 808.1918.

PREPARATION EXAMPLE 3

Preparation of Compound (149)

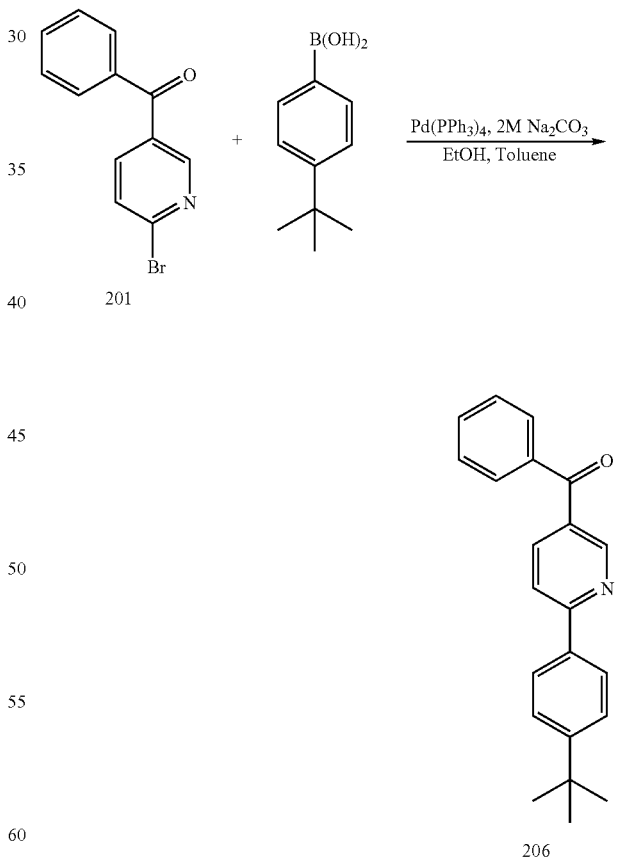

-continued

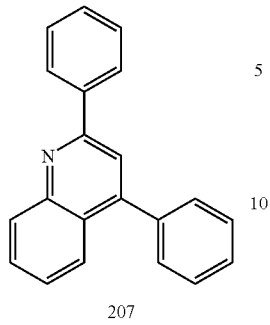

207

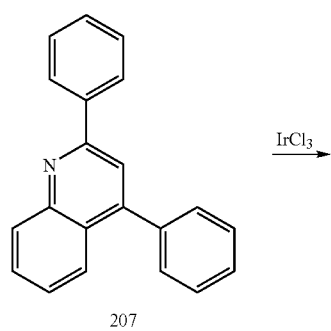

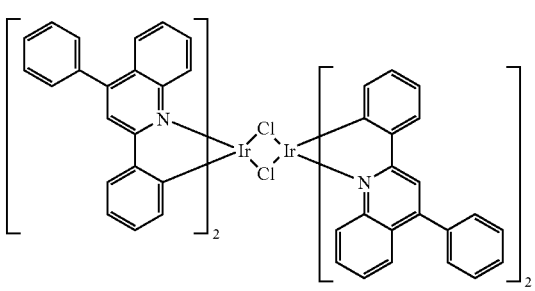

208

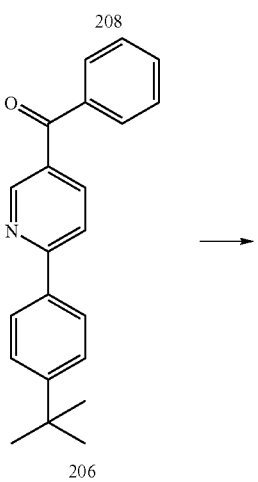

206

-continued

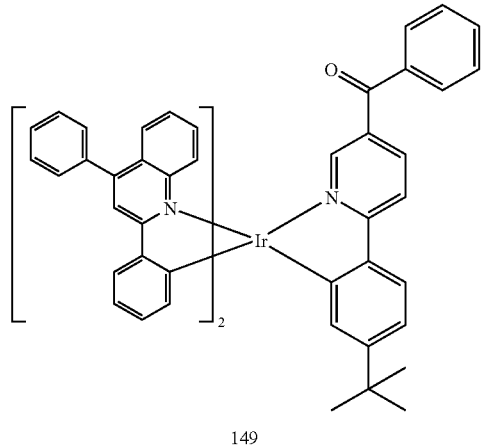

149

Preparation of Compound (206)

A 500 mL round-bottomed flask was charged with Compound (201) (18.0 g, 68.9 mmol), 4-t-butylphenylboronic acid (13.5 g, 75.8 mmol), toluene (160 mL), ethanol (80 mL) and Pd(PPh$_3$)$_4$ (3.18 g, 2.76 mmol) and aqueous 2 M Na$_2$CO$_3$ solution (80 mL). According to the same procedure as described in Preparation 1, obtained was Compound (206) (17.8 g, 56.5 mmol, yield: 82.0%).

Preparation of Compound (207)

Acetophenone (50 g, 416 mmol) and o-aminobenzophenone (82 g, 416 mmol) were stirred under reflux with concentrated sulfuric acid (4 mL) and glacial acetic acid (600 mL) for 24 hours. After cooling to room temperature, the reaction mixture was washed with cold concentrated ammonium hydroxide (450 mL) and distilled water (1.6 L). The precipitate was collected, and recrystallized from ethanol and water to obtain Compound (207) (81.9 g, 291 mmol).

Preparation of Compound (208)

Compound (207) (81.9 g, 291 mmol), iridium chloride (IrCl$_3$) (39.1 g, 131 mmol), 2-ethoxyethanol (600 mL) and distilled water (200 mL) were stirred under reflux for 24 hours, and the reaction mixture was cooled to room temperature. The precipitate was washed with water and methanol, and filtered, and recrystallized from hexane to obtain Compound (208) (67.8 g, 43 mmol).

Preparation of Compound (149)

Compound (208) (67.8 g, 43 mmol) and Compound (206) (40.7 g, 129 mmol), AgCF$_3$SO$_3$ (27.6 g, 107.5 mmol) and 2-methoxy ethylether (500 mL) were stirred under reflux for 12 hours. After cooling to room temperature, the reaction mixture was washed with water and methanol. The solid obtained was dissolved in methylene chloride, and purified via silica gel column chromatography to obtain the title compound, iridium complex (149) (32 g, 30 mmol, 35%) as red crystals.

mp. >350° C.

$^1$H NMR (300 MHz, CDCl$_3$): δ=9.03 (s, 1H), 8.1 (d, J=8.1 Hz, 2H), 8.01 (d, J=7.6 Hz, 1H), 8 (d, J=7.5 Hz, 2H), 7.91-7.81 (m, 6H), 7.7 (d, J=8.1 Hz, 2H), 7.6-7.4 (m, 13H), 7.3-7.2 (m, 12H), 1.34 (s, 9H)

HRMS (FAB) calcd for C$_{64}$H$_{48}$IrN$_3$O 1067.00: found, 1067.34

PREPARATION EXAMPLE 4-70

The organic electroluminescent compounds listed in Table 1 were prepared according to the procedures described in Preparation Example 1-3, and the $^1$H NMR, melting point (mp.) and MS/FAB data of the compounds are shown in Table 2.

TABLE 1

| compound No. | R$_1$ | R$_2$ | R$_3$ | R$_4$ | A | R$_5$, R$_6$ (B group) | L | n |
|---|---|---|---|---|---|---|---|---|
| 101 | phenyl | H | H | H | N | phenyl | acac (CH$_3$) | 2 |
| 102 | phenyl | H | H | H | N | 4-methylphenyl | acac (CH$_3$) | 2 |
| 103 | phenyl | H | H | H | N | 4-biphenyl | acac (CH$_3$) | 2 |
| 104 | phenyl | H | H | H | N | 4-tert-butylphenyl | acac (CH$_3$) | 2 |

TABLE 1-continued
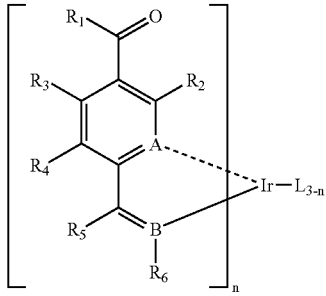
| compound No. | $R_1$ | $R_2$ | $R_3$ | $R_4$ | A---- | 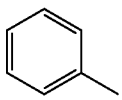 | L | n |
|---|---|---|---|---|---|---|---|---|
| 105 | 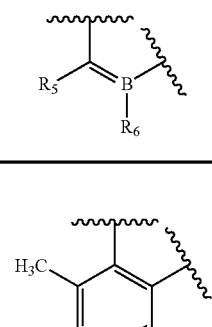 | H | H | H | N---- | 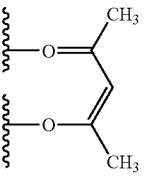 | 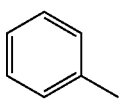 | 2 |
| 106 | 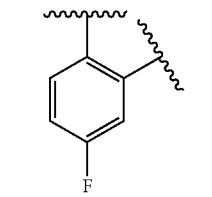 | H | H | H | N---- | 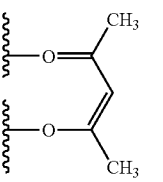 | 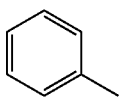 | 2 |
| 107 | 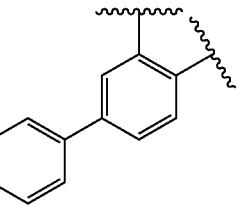 | H | H | H | N---- | 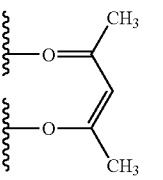 | 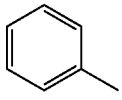 | 2 |
| 108 | 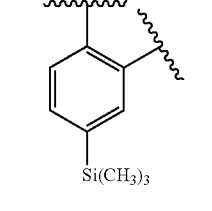 | H | H | H | N---- | 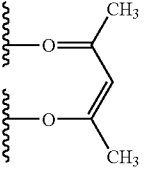 | 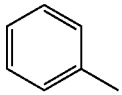 | 2 |
| 109 | 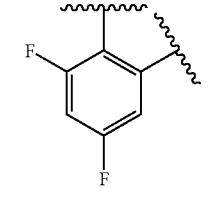 | H | H | H | N---- | 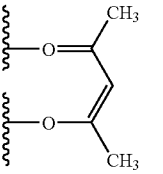 | | 2 |

TABLE 1-continued
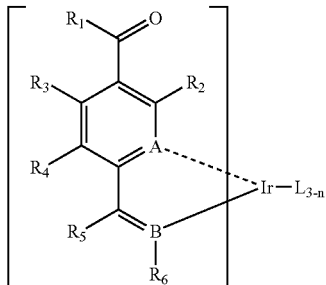
| compound No. | R₁ | R₂ | R₃ | R₄ | A---- | 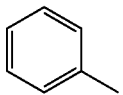 | L | n |
|---|---|---|---|---|---|---|---|---|
| 110 | 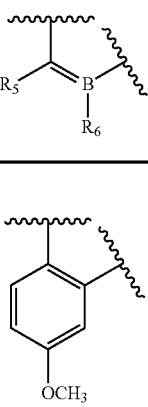 | H | H | H | N---- | 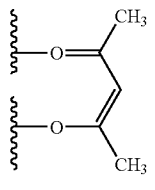 | 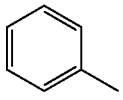 | 2 |
| 111 | 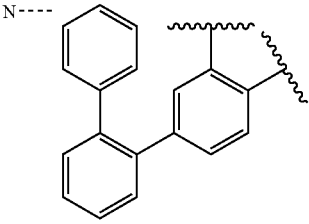 | H | H | H | N---- | 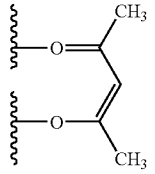 | 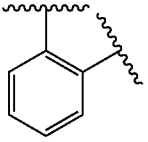 | 2 |
| 112 | 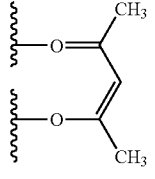 | H | H | H | N---- | 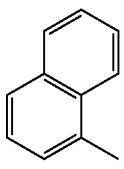 | 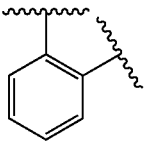 | 2 |
| 113 | 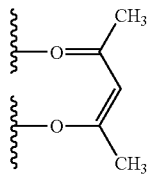 | H | H | H | N---- | 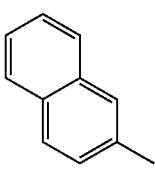 | 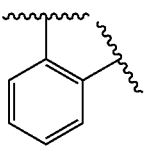 | 2 |
| 114 | 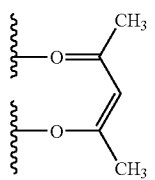 | H | H | H | N---- | | | 2 |

TABLE 1-continued
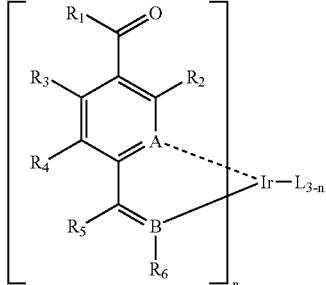
| compound No. | R₁ | R₂ | R₃ | R₄ | A---- | 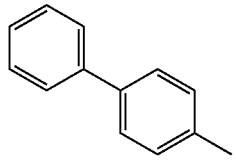 | L | n |
|---|---|---|---|---|---|---|---|---|
| 115 | 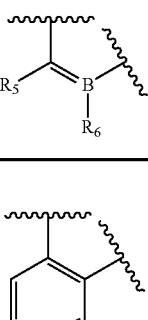 | H | H | H | N---- | 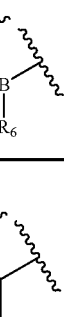 | 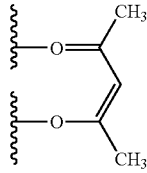 | 2 |
| 116 | 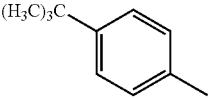 | H | H | H | N---- | 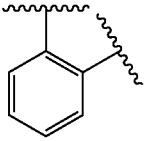 |  | 2 |
| 117 | 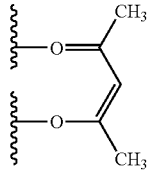 | H | H | H | N---- | 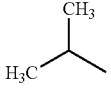 | 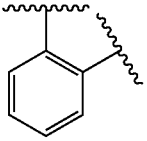 | 2 |
| 118 |  | H | H | H | N---- | 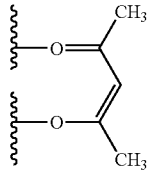 |  | 2 |
| 119 | 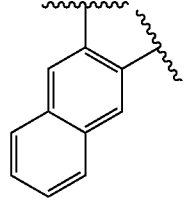 | H | H | H | N---- | 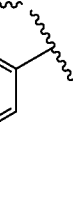 | 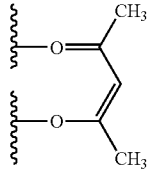 | 2 |

TABLE 1-continued

| compound No. | R₁ | R₂ | R₃ | R₄ | A---- | R₅, R₆, B | L | n |
|---|---|---|---|---|---|---|---|---|
| 120 | phenyl | H | H | H | N---- | 9,9-dimethylfluorene-2,3-diyl | acetylacetonate | 2 |
| 121 | isobutyl (CH(CH₃)₂CH) | H | H | H | N---- | =CH–C(phenyl)= | acetylacetonate | 2 |
| 122 | CH₃ | H | H | H | N---- | 2-methylphenylene | acetylacetonate | 2 |
| 123 | CH₃ | H | H | H | N---- | 4-tert-butylphenylene | acetylacetonate | 2 |
| 124 | CH₃ | H | H | H | N---- | biphenyl-diyl | acetylacetonate | 2 |

TABLE 1-continued
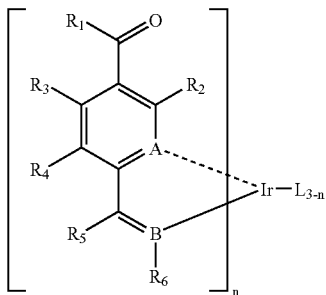
| compound No. | R$_1$ | R$_2$ | R$_3$ | R$_4$ | A---- | 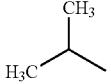 | L | n |
|---|---|---|---|---|---|---|---|---|
| 125 | 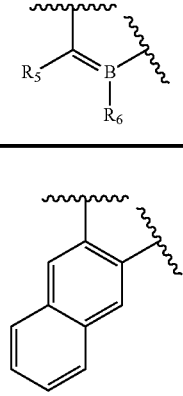 | H | H | H | N---- | 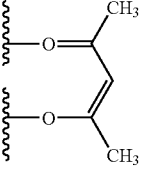 | 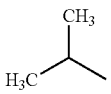 | 2 |
| 126 | 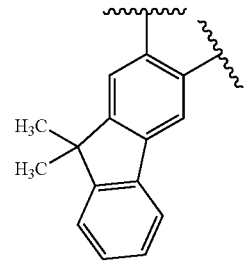 | H | H | H | N---- | 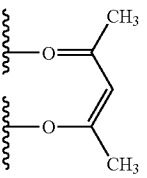 | 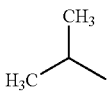 | 2 |
| 127 | 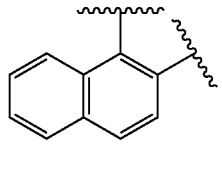 | H | H | H | N---- | 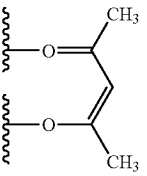 | 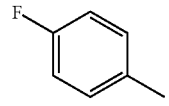 | 2 |
| 128 | 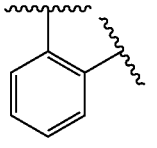 | H | H | H | N---- | 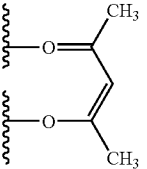 | 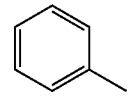 | 2 |
| 129 | 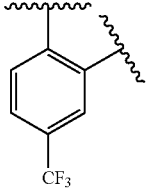 | H | H | H | N---- | 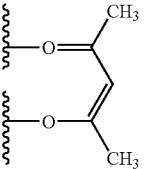 | | 2 |

TABLE 1-continued
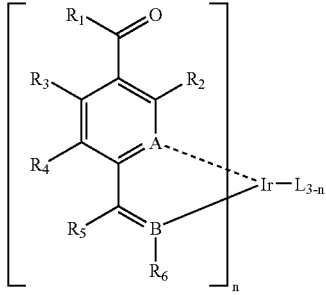
| compound No. | R₁ | R₂ | R₃ | R₄ | A---- | 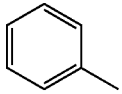 | L | n |
|---|---|---|---|---|---|---|---|---|
| 130 | 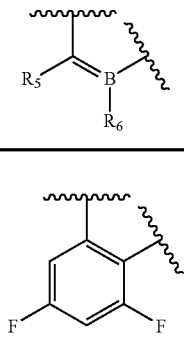 | H | H | H | N---- | 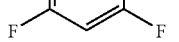 | 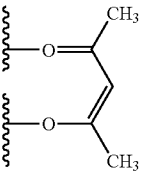 | 2 |
| 131 | 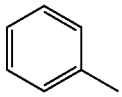 | H | H | H | C— | 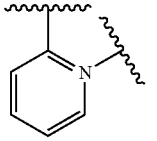 | 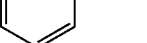 | 2 |
| 132 | H₃C— | H | H | H | C— | 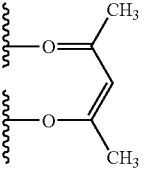 |  | 2 |
| 133 | 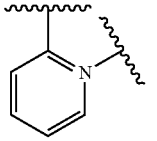 | H | H | H | N---- | 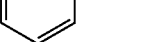 | 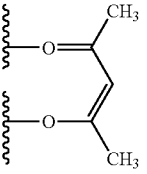 | 2 |
| 134 | 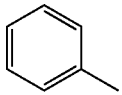 | H | H | H | N---- | 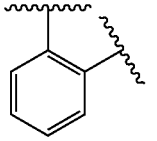 | 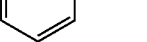 | 2 |

TABLE 1-continued
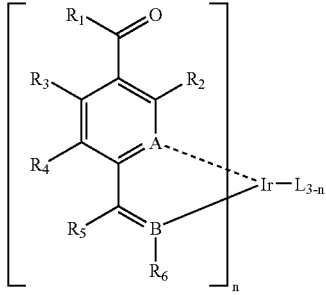
| compound No. | $R_1$ | $R_2$ | $R_3$ | $R_4$ | A---- | $R_5$ $R_6$ | L | n |
|---|---|---|---|---|---|---|---|---|
| 135 | 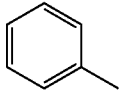 | H | H | H | N---- | 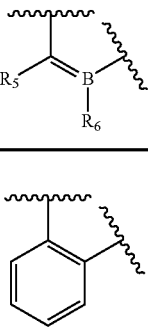 | 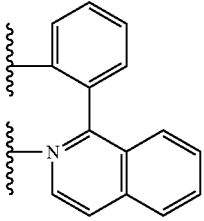 | 2 |
| 136 | 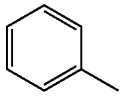 | H | H | H | N---- | 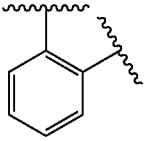 | 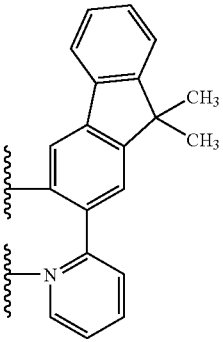 | 2 |
| 137 | 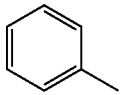 | H | H | H | N---- | 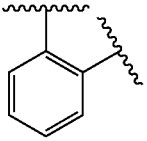 | 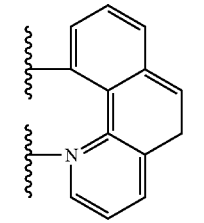 | 2 |
| 138 | 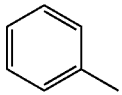 | H | H | H | N---- | 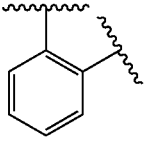 | 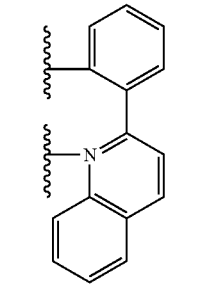 | 1 |

TABLE 1-continued

| compound No. | R₁ | R₂ | R₃ | R₄ | A---- | R₅⌇B⌇R₆ | L | n |
|---|---|---|---|---|---|---|---|---|
| 139 | phenyl | H | H | H | N---- | benzene | 2-phenylpyridine | 1 |
| 140 | phenyl | H | H | H | N---- | benzene | 1-phenylisoquinoline | 1 |
| 141 | phenyl | H | H | H | N---- | benzene | 9,9-dimethylfluorene-pyridine | 1 |
| 142 | phenyl | H | H | H | N---- | benzene | benzoquinoline | 1 |

TABLE 1-continued
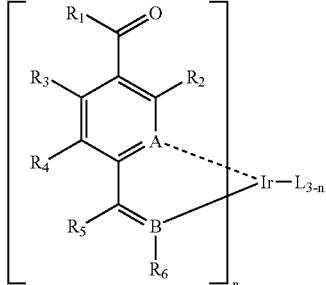
| compound No. | R₁ | R₂ | R₃ | R₄ | A---- | 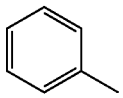 | L | n |
|---|---|---|---|---|---|---|---|---|
| 143 | 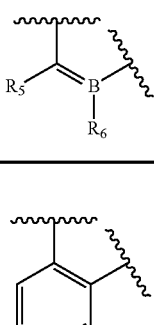 | H | H | H | N---- | 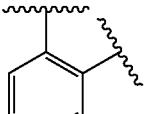 | 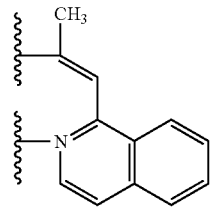 | 1 |
| 144 | H₃C— | H | H | H | N---- |  | 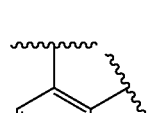 | 1 |
| 145 | 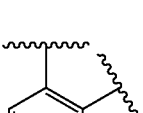 | H | H | H | N---- | 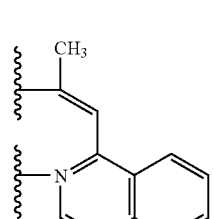 | 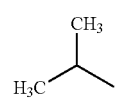 | 1 |
| 146 |  | H | H | H | N---- |  | 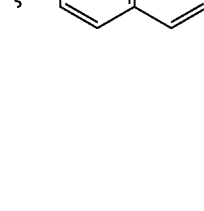 | 1 |

TABLE 1-continued

| compound No. | R₁ | R₂ | R₃ | R₄ | A---- | R₅  B  R₆ | L | n |
|---|---|---|---|---|---|---|---|---|
| 147 | phenyl | H | H | H | N---- | 4-tert-butylphenyl | 2-(quinolin-2-yl)phenyl | 1 |
| 148 | phenyl | H | H | H | N---- | 4-tert-butylphenyl | 2-(6-phenylquinolin-2-yl)phenyl | 1 |
| 149 | phenyl | H | H | H | N---- | 4-tert-butylphenyl | 2-(4-phenylquinolin-2-yl)phenyl | 1 |

TABLE 1-continued
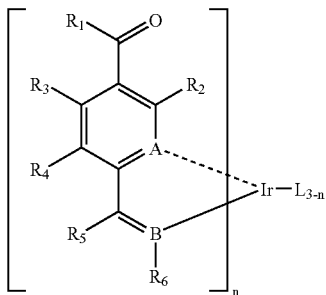
| compound No. | $R_1$ | $R_2$ | $R_3$ | $R_4$ | A---- | 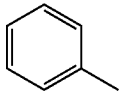 | L | n |
|---|---|---|---|---|---|---|---|---|
| 150 | 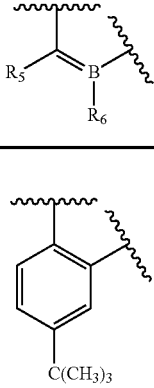 | H | H | H | N---- | 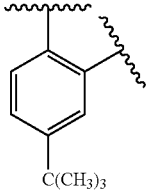 | 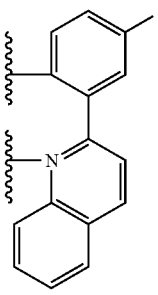 | 1 |
| 151 | 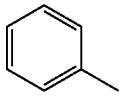 | H | H | H | N---- | 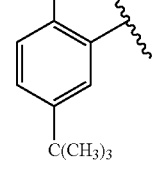 | 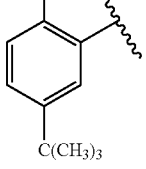 | 1 |
| 152 | 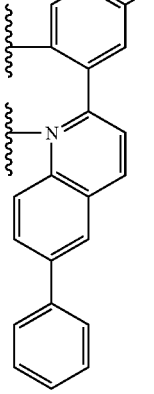 | H | H | H | N---- | 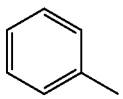 | 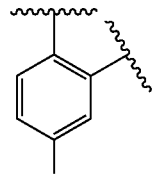 | 1 |

TABLE 1-continued

| compound No. | R₁ | R₂ | R₃ | R₄ | A---- | R₅ B R₆ | L | n |
|---|---|---|---|---|---|---|---|---|
| 153 | phenyl | H | H | H | N---- | 4-tert-butylphenyl | 1-(2-phenylvinyl)isoquinoline | 1 |
| 154 | phenyl | H | H | H | N---- | 4-tert-butylphenyl | 2-(2-phenylvinyl)quinoline | 1 |
| 155 | phenyl | H | H | H | N---- | 4-tert-butylphenyl | 2-phenylpyridine | 1 |
| 156 | phenyl | H | H | H | N---- | 4-tert-butylphenyl | 1-phenylisoquinoline | 1 |

TABLE 1-continued

| compound No. | R₁ | R₂ | R₃ | R₄ | A---- | R₅ B R₆ | L | n |
|---|---|---|---|---|---|---|---|---|
| 157 | phenyl | H | H | H | N---- | 2-(tert-butyl)phenyl with C(CH₃)₃ | 9,9-dimethylfluorene-pyridine | 1 |
| 158 | (H₃C)₃Si-phenyl | H | H | H | N---- | phenyl | acetylacetonate | 2 |
| 159 | phenyl | —CH₃ | H | H | N---- | phenyl | acetylacetonate | 2 |
| 160 | phenyl | H | —CH₃ | —CH₃ | N---- | phenyl | acetylacetonate | 2 |
| 161 | phenyl | H | H | H | N---- | phenyl | methyl-isoquinoline | 2 |

TABLE 1-continued
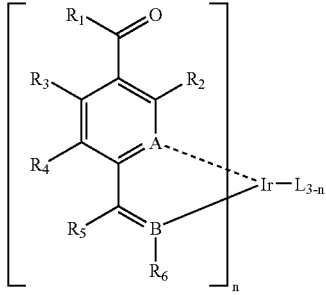
| compound No. | R₁ | R₂ | R₃ | R₄ | A---- | 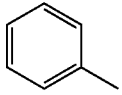 | L | n |
|---|---|---|---|---|---|---|---|---|
| 162 | 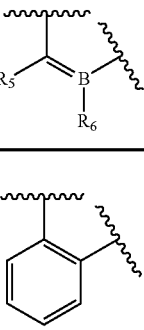 | H | H | H | N---- | 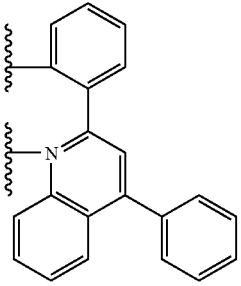 | 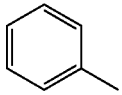 | 2 |
| 163 | 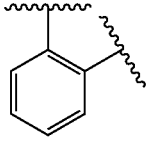 | H | H | H | N---- | 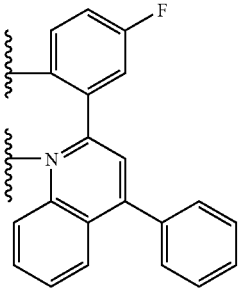 | 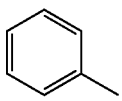 | 2 |
| 164 | 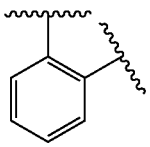 | H | H | H | N---- | 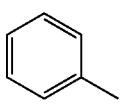 | — | 3 |
| 165 | 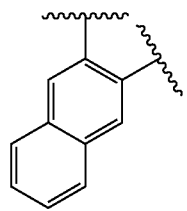 | H | H | H | N---- | 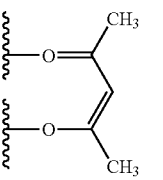 | (acac) | 2 |

TABLE 1-continued
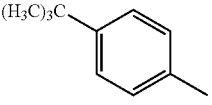
| compound No. | R₁ | R₂ | R₃ | R₄ | A---- | 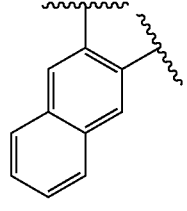 | L | n |
|---|---|---|---|---|---|---|---|---|
| 166 | 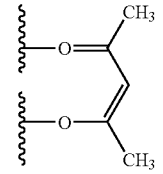 | H | H | H | N---- | 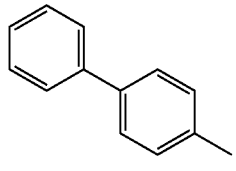 | 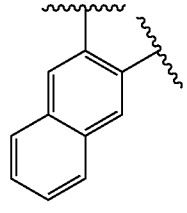 | 2 |
| 167 | 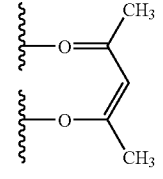 | H | H | H | N---- | 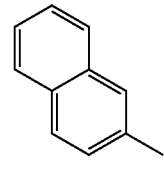 | 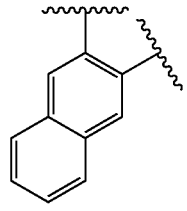 | 2 |
| 168 | 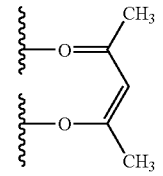 | H | H | H | N---- | 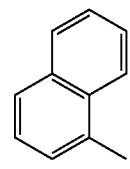 | 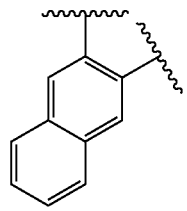 | 2 |
| 169 | 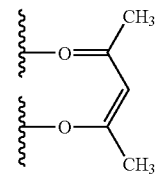 | H | H | H | N---- | | | 2 |
| 170 | H₃C— | H | H | H | N---- | 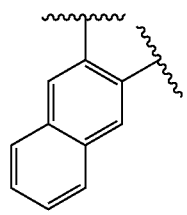 | 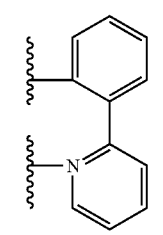 | 2 |

TABLE 1-continued
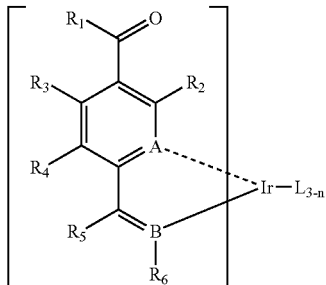
| compound No. | R₁ | R₂ | R₃ | R₄ | A---- | $\begin{matrix}R_5\\\phantom{=}\\B\\R_6\end{matrix}$ | L | n |
|---|---|---|---|---|---|---|---|---|
| 171 |  | H | H | H | N---- | 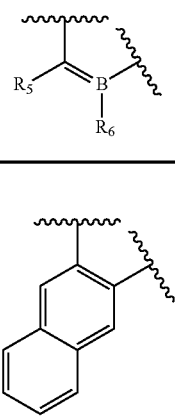 | — | 3 |
| 172 |  | H | H | H | N---- | 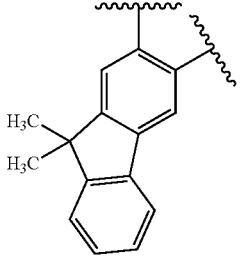 | 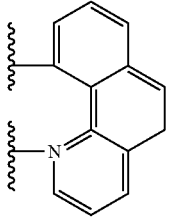 | 2 |
| 173 | 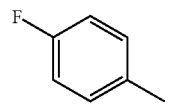 | H | H | H | N---- | 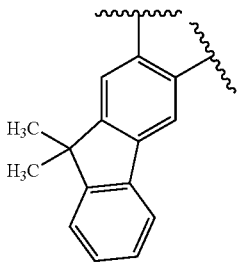 | 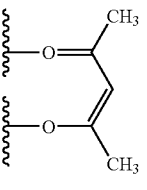 | 2 |
| 174 | 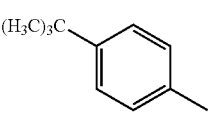 | H | H | H | N---- | 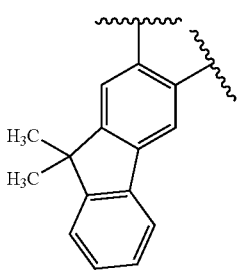 | 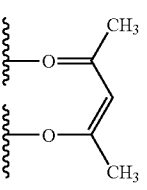 | 2 |

TABLE 1-continued
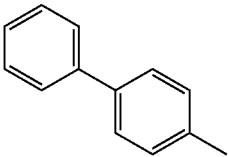
| compound No. | R₁ | R₂ | R₃ | R₄ | A---- | 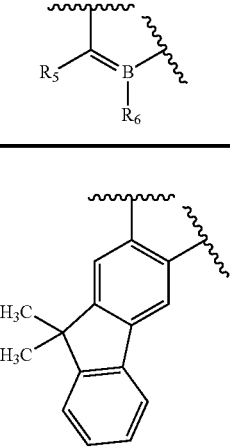 | L | n |
|---|---|---|---|---|---|---|---|---|
| 175 | 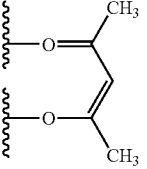 | H | H | H | N---- | 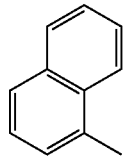 | 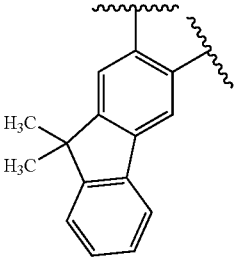 | 2 |
| 176 | 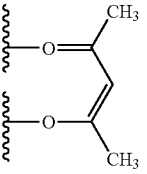 | H | H | H | N---- | 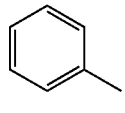 | 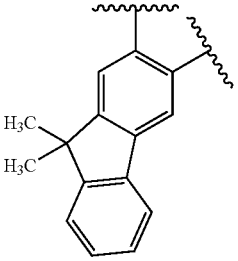 | 2 |
| 177 | 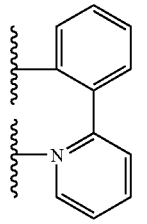 | H | H | H | N---- | 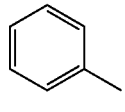 | 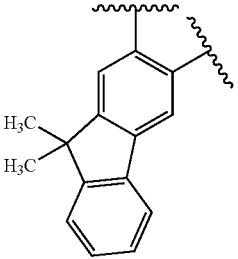 | 2 |
| 178 |  | H | H | H | N---- | (see below) | — | 3 |

TABLE 1-continued
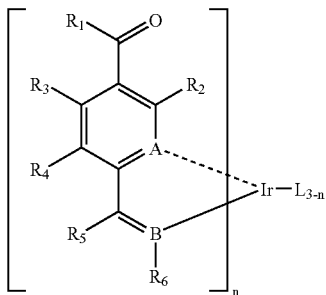
| compound No. | R₁ | R₂ | R₃ | R₄ | A---- | 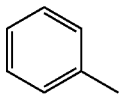 | L | n |
|---|---|---|---|---|---|---|---|---|
| 179 | 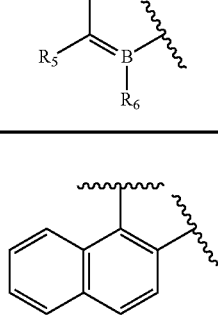 | H | H | H | N---- | 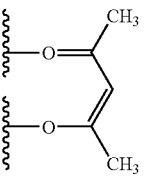 | 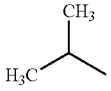 | 2 |
| 180 | 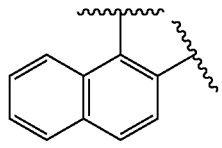 | —CH₃ | —CH₃ | —CH₃ | N---- | 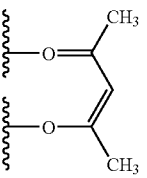 | 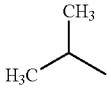 | 2 |
| 181 | 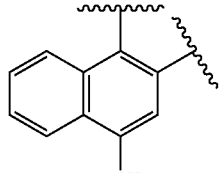 | H | H | H | N---- | 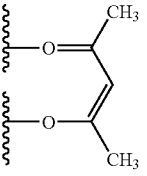 | 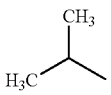 | 2 |
| 182 | 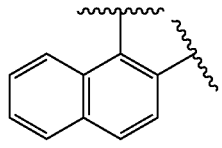 | H | H | H | N---- | 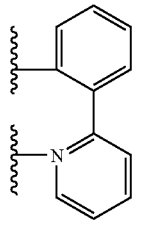 | 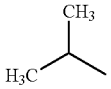 | 2 |
| 183 | 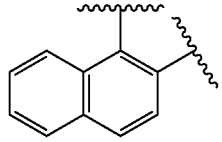 | H | H | H | N---- | 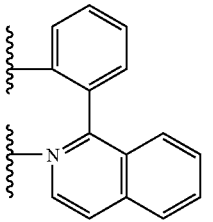 |  | 2 |

TABLE 1-continued
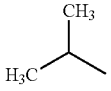
| compound No. | R₁ | R₂ | R₃ | R₄ | A---- | 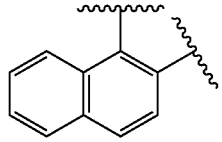 | L | n |
|---|---|---|---|---|---|---|---|---|
| 184 | 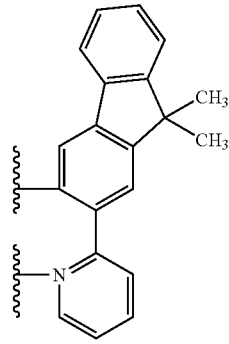 | H | H | H | N---- | 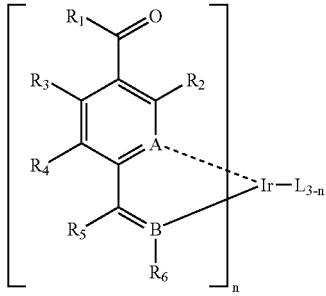 | 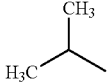 | 2 |
| 185 | 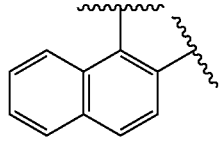 | H | H | H | N---- | 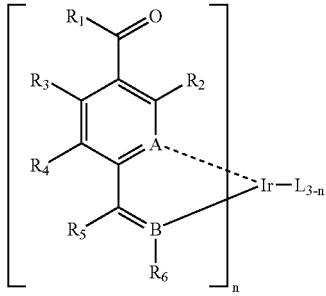 | — | 3 |
| 186 | 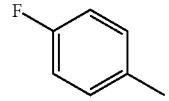 | H | H | H | C— | 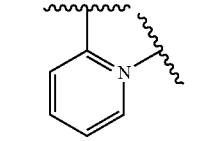 | 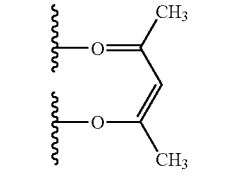 | 2 |
| 187 | 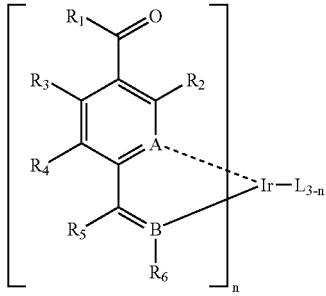 | H | H | H | C— | 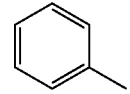 | 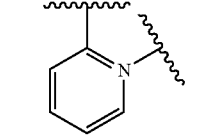 | 2 |
| 188 | 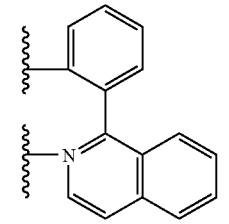 | H | H | H | C— | 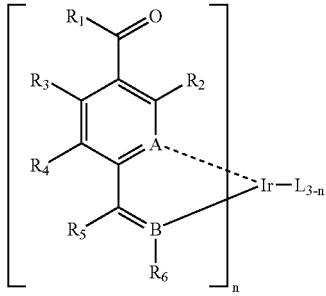 | 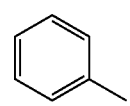 | 2 |

TABLE 1-continued

| compound No. | R₁ | R₂ | R₃ | R₄ | A---- | [R₅=B with R₆ structure] | L | n |
|---|---|---|---|---|---|---|---|---|
| 189 | phenyl | H | H | H | C— | pyridyl | 1-isoquinolinyl-2-methylvinyl | 2 |
| 190 | isobutyl | H | H | H | C— | 5-methylpyridyl | acetylacetonate | 2 |
| 191 | ethyl | H | H | H | C— | 5-methylpyridyl | 2-(2-pyridyl)phenyl | 2 |
| 192 | phenyl | H | H | H | C— | pyridyl | — | 3 |
| 193 | phenyl | H | H | H | N---- | methyl-phenyl vinyl B | acetylacetonate | 2 |

TABLE 1-continued
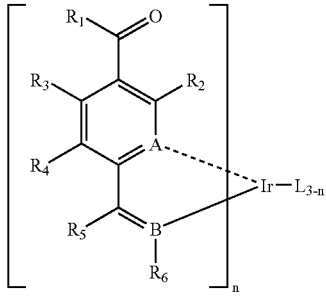
| compound No. | R₁ | R₂ | R₃ | R₄ | A---- | 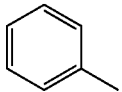 | L | n |
|---|---|---|---|---|---|---|---|---|
| 194 | 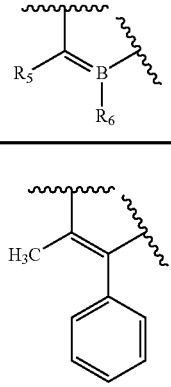 | H | H | H | N---- | 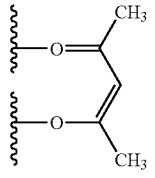 |  | 2 |
| 195 | H₃C— | H | H | H | N---- | 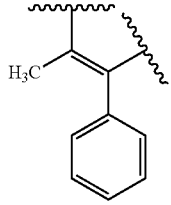 | 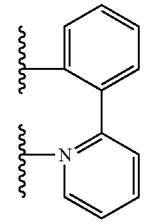 | 2 |
| 196 | 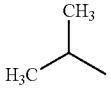 | H | H | H | N---- | 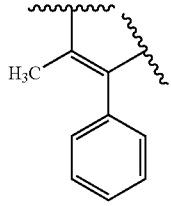 | 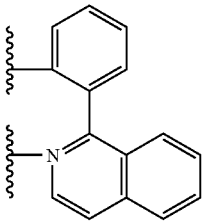 | 2 |
| 197 | 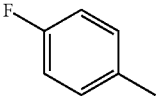 | H | H | H | N---- | 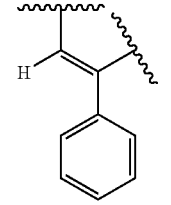 | 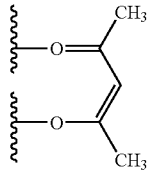 | 2 |
| 198 | 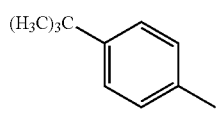 | H | H | H | N---- | 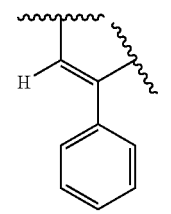 | 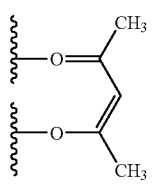 | 2 |

TABLE 1-continued

| compound No. | R₁ | R₂ | R₃ | R₄ | A---- | R₅  R₆ | L | n |
|---|---|---|---|---|---|---|---|---|
| 199 | biphenyl (4-phenylphenyl) | H | H | H | N---- | CH=C(phenyl)- | acetylacetonate (O-C(CH₃)=CH-C(CH₃)=O) | 2 |
| 200 | isopropyl (isobutyl, (CH₃)₂CHCH₂-) | H | H | H | N---- | CH=C(phenyl)- | — | 3 |

TABLE 2

| Compound No. | $^1$H NMR (CDCl₃, 300 MHz) | MS/FAB found | MS/FAB calculated |
|---|---|---|---|
| 101 | δ = 8.89 (d, J = 1.2 Hz, 2H), 8.30 (dd, J = 1.8 Hz, 8.4 Hz, 2H), 7.98 (d, J = 8.7 Hz, 2H), 7.83-7.80 (m, 4H), 7.65-7.58 (m, 4H) 7.53-7.48 (m, 4H), 6.86 (td, J = 1.2 Hz, 7.5 Hz, 2H), 6.74 (td, J = 1.5 Hz, 7.5 Hz, 2H), 6.30 (dd, J = 1.2 Hz, 7.8 Hz, 2H), 5.29 (s, 1H), 1.55 (s, 6H). | 808.1910 | 808.1913 |
| 102 | δ = 8.83 (d, J = 2.0 Hz, 2H), 8.27 (dd, J = 2.0 Hz, 8.5 Hz, 2H), 7.93 (d, J = 8.6 Hz, 2H), 7.82-7.79 (m, 4H), 7.63-7.57 (m, 2H), 7.55-7.47 (m, 6H), 6.68 (dd, J = 1.6 Hz, 7.9 Hz, 2H), 6.10 (s, 2H), 5.28 (s, 1H), 2.08 (s, 6H), 1.55 (s, 6H). | 836.2228 | 836.2226 |
| 103 | δ = 8.92 (d, J = 1.3 Hz, 2H), 8.29 (dd, J = 2.0 Hz, 8.5 Hz, 2H), 8.00 (d, J = 8.7 Hz, 2H), 7.81 (dd, J = 1.3 Hz, 8.3 Hz, 4H), 7.70 (d, J = 8.1 Hz, 2H), 7.63-7.58 (m, 2H), 7.51-7.46 (m, 4H), 7.35-7.19 (m, 10H), 7.11 (dd, J = 1.8 Hz, 8.1 Hz, 2H), 6.54 (d, J = 1.6 Hz, 2H), 5.28 (s, 1H), 1.57 (s, 6H). | 960.2545 | 960.2539 |
| 104 | δ = 8.89 (dd, J = 0.6 Hz, 1.4 Hz, 2H), 8.26 (dd, J = 2.0 Hz, 8.5 Hz, 2H), 7.92 (d, J = 8.1 Hz, 2H), 7.83 (dd, J = 1.4 Hz, 8.3 Hz, 4H), 7.61-7.46 (m, 8H), 6.90 (dd, J = 1.9 Hz, 8.3 Hz, 2H), 6.30 (d, J = 1.8 Hz, 2H), 5.12 (s, 1H), 1.47 (s, 6H), 1.07 (s, 18H). | 920.3160 | 920.3165 |
| 105 | δ = 8.80 (d, J = 2.0 Hz, 2H), 8.27 (dd, J = 2.2 Hz, 8.5 Hz, 2H), 7.93 (d, J = 8.6 Hz, 2H), 7.82-7.79 (m, 4H), 7.63-7.58 (m, 2H), 7.55-7.47 (m, 6H), 6.68 (dd, J = 1.6 Hz, 7.9 Hz, 2H), 6.10 (s, 2H), 5.28 (s, 1H), 2.08 (s, 6H), 1.55 (s, 6H). | 836.2228 | 836.2226 |
| 106 | δ = 8.81 (d, J = 2.0 Hz, 2H), 8.30 (dd, J = 2.0 Hz, 8.5 Hz, 2H), 7.92 (d, J = 8.6 Hz, 2H), 7.80 (d, J = 7.0 Hz, 4H), 7.67-7.60 (m, 4H), 7.54-7.49 (m, 4H), 6.61 (td, J = 2.5 Hz, 8.7 Hz, 2H), 5.91 (dd, J = 2.5 Hz, 9.5 Hz, 2H), 5.28 (s, 1H), 1.57 (s, 6H). | 844.1711 | 844.1725 |

TABLE 2-continued

| Compound No. | ¹H NMR (CDCl₃, 300 MHz) | MS/FAB found | MS/FAB calculated |
|---|---|---|---|
| 107 | δ = 8.92 (d, J = 1.3 Hz, 2H), 8.29 (dd, J = 2.0 Hz, 8.5 Hz, 2H), 8.00 (d, J = 8.2 Hz, 2H), 7.81 (dd, J = 1.3 Hz, 8.3 Hz, 4H), 7.70 (d, J = 8.1 Hz, 2H), 7.63-7.59 (m, 2H), 7.51-7.46 (m, 4H), 7.35-7.25 (m, 10H), 7.16 (dd, J = 1.8 Hz, 8.1 Hz, 2H), 6.54 (d, J = 1.6 Hz, 2H), 5.28 (s, 1H), 1.55 (s, 6H). | 960.2545 | 960.2539 |
| 108 | δ = 8.89 (dd, J = 0.6 Hz, 1.4 Hz, 2H), 8.26 (dd, J = 2.0 Hz, 8.5 Hz, 2H), 7.92 (d, J = 8.1 Hz, 2H), 7.83 (dd, J = 1.4 Hz, 8.3 Hz, 4H), 7.61-7.46 (m, 8H), 6.90 (dd, J = 1.9 Hz, 8.3 Hz, 2H), 6.30 (d, J = 1.8 Hz, 2H), 5.12 (s, 1H), 1.47 (s, 6H), 1.07 (s, 9H), 0.66 (s, 9H). | 952.28 | 952.27 |
| 109 | δ = 8.81 (d, J = 1.9 Hz, 2H), 8.41-8.31 (m, 4H), 7.82-7.79 (m, 4H), 7.64 (t, J = 7.4 Hz, 2H), 7.53 (t, J = 7.6 Hz, 4H), 6.43-6.36 (m, 2H), 5.70 (dd, J = 2.3 Hz, 8.6 Hz, 2H), 5.31 (s, 1H), 1.59 (s, 6H). | 880.1533 | 880.1536 |
| 110 | δ = 8.80 (d, J = 2.0 Hz, 2H), 8.25 (dd, J = 2.0 Hz, 8.6 Hz, 2H), 7.84 (d, J = 8.7 Hz, 2H), 7.79 (d, J = 7.7 Hz, 4H), 7.61 (d, J = 8.7 Hz, 4H), 7.53-7.48 (m, 4H), 6.46 (dd, J = 2.5 Hz, 8.6 Hz, 2H), 5.79 (d, J = 2.5 Hz, 2H), 5.28 (s, 1H), 3.56 (s, 6H), 1.55 (s, 6H). | 868.2139 | 868.2125 |
| 111 | δ = 8.92 (d, J = 1.3 Hz, 2H), 8.29 (dd, J = 2.0 Hz, 8.5 Hz, 2H), 8.00 (d, J = 8.7 Hz, 2H), 7.81 (dd, J = 1.3 Hz, 8.3 Hz, 4H), 7.70 (d, J = 8.1 Hz, 2H), 7.63-7.58 (m, 2H), 7.51-7.46 (m, 6H), 7.35-7.19 (m, 13H), 7.11 (dd, J = 1.8 Hz, 8.1 Hz, 2H), 6.54 (d, J = 1.6 Hz, 2H), 5.28 (s, 1H), 1.57 (s, 6H). | 1112.30 | 1112.32 |
| 112 | δ = 9.06 (d, J = 2.0 Hz, 2H), 8.26 (dd, J = 2.0 Hz, 8.6 Hz, 2H), 7.93 (d, J = 8.7 Hz, 2H), 7.62 (d, J = 7.7 Hz, 2H), 6.88-6.83 (m, 2H), 6.76-6.70 (m, 2H), 6.28 (d, J = 7.7 Hz, 2H), 5.29 (s, 1H), 2.60 (s, 6H), 1.84 (s, 6H). | 684.1585 | 684.1600 |
| 113 | δ = 8.61 (d, J = 2.0 Hz, 2H), 8.38 (dd, J = 2.0 Hz, 8.5 Hz, 2H), 8.04 (d, J = 7.8 Hz, 2H), 8.00 (d, J = 8.2 Hz, 2H), 7.95 (d, J = 8.2 Hz, 2H), 7.90 (d, J = 7.8 Hz, 2H), 7.61-7.58 (m, 4H), 7.57-7.47 (m, 6H), 6.82 (td, J = 1.2 Hz, 7.5 Hz, 2H), 6.71 (td, J = 1.4 Hz, 7.4 Hz, 2H), 6.24 (dd, J = 0.8 Hz, 7.6 Hz, 2H), 4.65 (s, 1H), 1.19 (s, 6H). | 908.2236 | 908.2226 |
| 114 | δ = 8.92 (d, J = 1.4 Hz, 2H), 8.32 (dd, J = 2.0 Hz, 8.5 Hz, 2H), 8.23 (s, 2H), 8.00 (d, J = 8.2 Hz, 2H), 7.96-7.90 (m, 8H), 7.66-7.59 (m, 6H), 6.87 (td, J = 1.2 Hz, 7.5 Hz, 2H), 6.76 (td, J = 1.4 Hz, 7.4 Hz, 2H), 6.32 (dd, J = 1.0 Hz, 7.6 Hz, 2H), 5.18 (s, 1H), 1.22 (s, 6H). | 908.2236 | 908.2226 |
| 115 | δ = 8.94 (d, J = 2.0 Hz, 2H), 8.31 (dd, J = 2.0 Hz, 8.5 Hz, 2H), 8.00 (d, J = 8.3 Hz, 2H), 7.90 (d, J = 8.3 Hz, 4H), 7.72 (d, J = 8.3 Hz, 4H), 7.66-7.60 (m, 6H), 7.51-7.38 (m, 6H), 6.87 (td, J = 1.0 Hz, 7.5 Hz, 2H), 6.76 (td, J = 1.3 Hz, 7.5 Hz, 2H), 6.33 (d, J = 7.5 Hz, 2H), 5.31 (s, 1H), 1.57 (s, 6H). | 960.2555 | 960.2539 |
| 116 | δ = 8.91 (d, J = 2.0 Hz, 2H), 8.31 (dd, J = 2.0 Hz, 8.5 Hz, 2H), 7.98 (d, J = 8.7 Hz, 2H), 7.77 (d, J = 8.4 Hz, 4H), 7.64 (dd, J = 1.2 Hz, 7.8 Hz, 2H), 7.51 (d, J = 8.4 Hz, 4H), 6.86 (td, J = 1.2 Hz, 7.5 Hz, 2H), 6.74 (td, J = 1.4 Hz, 7.4 Hz, 2H), 6.30 (dd, J = 0.8 Hz, 7.6 Hz, 2H), 5.28 (s, 1H), 1.56 (s, 6H), 1.35 (s, 18H). | 920.3166 | 920.3165 |
| 117 | δ = 9.09 (d, J = 1.8 Hz, 2H), 8.28 (dd, J = 1.8 Hz, 8.4 Hz, 2H), 7.94 (d, J = 8.4 Hz, 2H), 7.63 (dd, = 1.2 Hz, 8.4 Hz, 2H), 6.87-6.83 (m, 2H), 6.76-6.71 (m, 2H), 6.30 (d, = 0.9 Hz, 7.8 Hz, 2H), 5.29 (s, 1H), 3.42 (m, 2H), 1.83 (s, 6H), 1.27 (d, = 7.2 Hz, 12H). | 740.2222 | 740.2226 |
| 118 | δ = 9.22 (d, J = 1.5 Hz, 2H), 8.41 (dd, J = 2.0 Hz, 8.6 Hz, 2H), 8.24 (d, J = 8.4 Hz, 2H), 8.19 (s, 2H), 7.67 (d, J = 7.5 Hz, 2H), 7.26 (d, J = 9.4 Hz, 2H), 7.21-7.18 (m, 2H), 7.16-7.13 (m, 2H), 6.61 (s, 2H), 5.32 (s, 1H), 2.68 (s 6H), 1.88 (s, 6H). | 784.1920 | 784.1913 |
| 119 | δ = 9.14, (d, J = 2.0 Hz, 2H), 8.40 (dd, J = 2.0 Hz, 8.6 Hz, 2H), 8.14 (d, J = 8.8 Hz, 2H), 7.83 (s, 2H), 7.40 (d, J = 7.5 Hz, 2H), 7.36 (d, J = 7.5 Hz, 2H), 7.27 (dd, J = 1.2 Hz, 7.4 Hz, 2H), 7.22-7.19 (m, 2H), 6.72 (s, 2H), 5.43 (s, 1H), 2.66 (s, 6H), 1.91 (s, 6H), 1.52 (s, 6H), 1.46 (s, 6H). | 916.2869 | 916.2852 |
| 120 | δ = 9.14, (d, J = 2.0 Hz, 2H), 8.40 (dd, J = 2.0 Hz, 8.6 Hz, 2H), 8.14 (d, J = 8.8 Hz, 2H), 7.83 (s, 2H), 7.81-7.45 (m, 5H), 7.40 (d, J = 7.5 Hz, 2H), 7.36 (d, J = 7.5 Hz, 2H), 7.27 (dd, J = 1.2 Hz, 7.4 Hz, 2H), 7.22-7.19 (m, 2H), 6.72 (s, 2H), 5.43 (s, 1H), 2.66 (s, 6H), 1.91 (s, 6H), 1.52 (s, 6H), 1.46 (s, 6H). | 1040.32 | 1040.23 |
| 121 | δ = 8.28 (d, J = 2.1 Hz, 2H), 7.89 (dd, J = 2.1 Hz, 8.7 Hz, 2H), 7.22 (d, J = 8.1 Hz, 6H), 6.95-6.91 (m, 6H), 6.90-6.87 (m, 6H), 5.17 (s, 1H), 3.08 (m, 2H), 1.87 (s, 6H), 1.12 (d, J = 6.6 Hz, 6H), 1.03 (d, J = 6.6 Hz, 6H). | 792.2558 | 792.2539 |
| 122 | δ = 9.06 (d, J = 2.0 Hz, 2H), 8.26 (dd, J = 2.0 Hz, 8.6 Hz, 2H), 7.93 (d, J = 8.7 Hz, 2H), 7.62 (d, J = 7.7 Hz, 2H), 6.88-6.85 (m, | 712.1913 | 711.8311 |

TABLE 2-continued

| Compound No. | $^1$H NMR (CDCl$_3$, 300 MHz) | MS/FAB found | MS/FAB calculated |
|---|---|---|---|
| | 1H), 6.76-6.70 (m, 2H), 6.28 (d, J = 7.7 Hz, 2H), 5.29 (s, 1H), 2.60 (s, 6H), 2.35 (s, 3H), 1.84 (s, 6H). | | |
| 123 | δ = 9.09 (d, J = 2.0 Hz, 2H), 8.24 (dd, J = 2.0 Hz, 8.6 Hz, 2H), 7.87 (d, J = 8.5 Hz, 2H), 7.54 (d, J = 8.3 Hz, 2H), 6.89 (dd, J = 1.9 Hz, 8.3 Hz, 2H), 6.23 (d, J = 1.9 Hz, 2H), 5.27 (s, 1H), 2.60 (s, 6H), 1.85 (s, 6H), 1.03 (s, 18H). | 796.2852 | 796.2855 |
| 124 | δ = 9.10 (d, J = 2.0 Hz, 2H), 8.29 (dd, J = 2.0 Hz, 8.6 Hz, 2H), 7.97 (d, J = 8.7 Hz, 2H), 7.70 (d, J = 8.2 Hz, 2H), 7.30-7.27 (m, 10H), 7.11 (dd, J = 1.8 Hz, 8.1 Hz, 2H), 6.50 (d, J = 1.7 Hz, 2H), 5.33 (s, 1H), 2.63 (s, 6H), 1.87 (s, 6H). | 836.2196 | 838.2226 |
| 125 | δ = 9.22 (d, J = 1.8 Hz, 2H), 8.40 (dd, J = 1.8 Hz, 8.7 Hz, 2H), 8.22 (d, J = 8.7 Hz, 2H), 8.16 (s, 2H), 7.65 (d, J = 7.8 Hz, 2H), 7.24-7.11 (m, 6H), 6.61 (s, 2H), 5.33 (s, 1H), 3.47 (m, 2H), 1.84 (s, 6H), 1.30 (d, J = 6.6 Hz, 12H). | 840.2556 | 840.2542 |
| 126 | δ = 9.15 (d, J = 2.1 Hz, 2H), 8.35 (dd, J = 2.1 Hz, 8.7 Hz, 2H), 8.06 (d, J = 8.7 Hz, 2H), 7.70 (s, 2H), 7.32-7.28 (m, 4H), 7.22-7.15 (m, 4H), 6.64 (s, 2H), 5.33 (s, 1H), 3.48 (m, 2H), 1.86 (s, 6H), 1.43 (d, J = 10 Hz, 12H), 1.29 (d, J = 6.6 Hz, 12H). | 972.3484 | 972.3478 |
| 127 | δ = 9.13 (d, J = 1.8 Hz, 2H), 8.62 (d, J = 8.7 Hz, 2H), 8.53 (d, J = 8.7 Hz, 2H), 8.36 (dd, J = 2.1 Hz, 8.7 Hz, 2H), 7.65-7.62 (m, 2H), 7.52-7.47 (m, 2H), 7.31-7.26 (m, 2H), 7.08 (d, J = 8.4 Hz, 2H), 6.35 (d, 8.4 Hz, 2H), 5.33 (s, 1H), 3.42 (m, 2H), 1.84 (s, 6H), 1.27 (d, J = 6.6 Hz, 6H), 1.26 (d, J = 6.6 Hz, 6H). | 840.2535 | 840.2542 |
| 128 | δ = 8.86 (d, J = 2.0 Hz, 2H), 8.26 (dd, J = 2.0 Hz, 8.5 Hz, 2H), 7.99 (d, J = 8.6 Hz, 2H), 7.86 (dd, J = 5.4 Hz, 8.7 Hz, 4H), 7.64 (dd, J = 1.1 Hz, 7.8 Hz, 2H), 7.19 (t, J = 8.5 Hz, 4H), 6.82 (td, J = 1.1 Hz, 7.5 Hz, 2H), 6.75 (td, J = 1.3 Hz, 7.4 Hz, 2H), 6.29 (dd, J = 1.1 Hz, 7.5 Hz, 2H), 5.29 (s, 1H), 1.59 (s, 6H). | 844.1733 | 844.1725 |
| 129 | δ = 8.85 (d, J = 1.9 Hz, 2H), 8.36 (dd, J = 2.0 Hz, 8.4 Hz, 2H), 8.08 (d, J = 8.6 Hz, 2H), 7.82-7.79 (m, 4H), 7.74 (d, J = 8.1 Hz, 2H), 7.63-7.60 (m, 2H), 7.54-7.49 (m, 4H), 7.14 (d, J = 7.7 Hz, 2H), 6.50 (s, 2H), 5.23 (s, 1H), 1.53 (s, 6H). | 944.1659 | 944.1661 |
| 130 | δ = 8.79 (d, J = 2.0 Hz, 2H), 8.29 (dd, J = 2.0 Hz, 8.5 Hz, 2H), 7.89 (d, J = 8.6 Hz, 2H), 7.81-7.78 (m, 4H), 7.63-7.60 (m, 2H), 7.54-7.49 (m, 4H), 7.30 (dd, J = 2.3 Hz, 9.2 Hz, 2H), 6.29 (td, J = 2.3 Hz, 9.2 Hz, 2H), 5.29 (s, 1H), 1.54 (s, 6H). | 880.1533 | 880.1536 |
| 131 | δ = 8.51-8.49 (m, 2H), 7.86 (d, J = 8.1 Hz, 2H), 7.68 (dd, J = 1.5 Hz, 7.5 Hz, 2H), 7.63 (d, J = 8.4 Hz, 2H), 7.57-7.54 (m, 4H), 7.49-7.44 (m, 2H), 7.34-7.28 (m, 6H), 7.16-7.11 (m, 2H), 6.59 (d, J = 1.5 Hz, 2H), 5.25 (s, 1H), 1.80 (s, 6H). | 808.1918 | 808.1913 |
| 132 | δ = 8.58 (dd, J = 0.8 Hz, 5.7 Hz, 2H), 7.96 (d, J = 7.8 Hz, 2H), 7.87-7.81 (m, 2H), 7.61 (d, J = 8.1 Hz, 2H), 7.41 (dd, J = 1.8 Hz, 8.1 Hz, 2H), 7.31-7.28 (m, 2H), 7.65 (d, J = 1.8 Hz, 2H), 5.25 (s, 1H), 2.27 (s, 6H), 1.80 (s, 6H). | 684.1606 | 684.1600 |
| 133 | δ = 9.03 (s, 2H), 8.1-8.0 (m, 6H), 7.91 (d, J = 7.5 Hz, 2H), 7.81-7.79 (m, 5H), 7.7-7.6 (m, 3H), 7.54-7.4 (m, 7H), 7.38-7.32 (m, 9H) | 913.23 | 913.05 |
| 134 | δ = 9.05 (s, 2H), 8.56 (d, J = 2.8 Hz, 1H), 8.1-8.0 (m, 5H), 7.91 (d, J = 8.3 Hz, 2H), 7.81 (d, J = 7.6 Hz, 4H), 7.54-7.45 (m, 8H), 7.3-6.98 (m, 10H). | 863.21 | 862.99 |
| 135 | δ = 9.03 (s, 2H), 8.5 (d, J = 2.5 Hz, 2H), 8.1-8.0 (m, 5H), 7.95-7.9 (m, 3H), 7.81-7.7 (m, 5H), 7.6-7.48 (m, 8H), 7.3-7.1 (m, 10H). | 913.23 | 913.05 |
| 136 | δ = 9.03 (s, 2H), 8.56 (d, J = 6.2 Hz, 1H), 8.3 (d, J = 7.2 Hz, 1H), 8.1-8.0 (m, 4H), 7.91-7.81 (m, 8H), 7.6-7.4 (m, 10H), 7.38-7.22 (m, 8H), 1.67 (s, 6H). | 979.27 | 979.15 |
| 137 | δ = 9.03 (s, 2H), 8.8 (d, J = 7.2 Hz, 1H), 8.1-8.0 (m, 5H), 7.91 (d, J = 7.5 Hz, 2H), 7.81-7.7 (m, 6H), 7.54-7.4 (m, 7H), 7.35-7.3 (m, 9H). | 887.21 | 887.01 |
| 138 | δ = 9.03 (s, 1H), 8.1-8.0 (m, 6H), 7.91 (d, J = 7.5 Hz, 1H), 7.81-7.79 (m, 4H), 7.7-7.6 (m, 6H), 7.54-7.4 (m, 5H), 7.38-7.32 (m, 9H). | 859.22 | 859.00 |
| 139 | δ = 9.05 (s, 1H), 8.56 (d, J = 2.8 Hz, 2H), 8.1-8.0 (m, 4H), 7.91 (d, J = 8.3 Hz, 1H), 7.81 (d, J = 7.6 Hz, 2H), 7.54-7.45 (m, 7H), 7.3-6.98 (m, 11H). | 759.89 | 759.19 |
| 140 | δ = 9.03 (s, 1H), 8.5 (d, J = 2.5 Hz, 2H), 8.1-8.0 (m, 4H), 7.95-7.9 (m, 3H), 7.81-7.7 (m, 4H), 7.6-7.48 (m, 7H), 7.3-7.1 (m, 11H). | 859.22 | 859.00 |
| 141 | δ = 9.03 (s, 1H), 8.56 (d, J = 6.2 Hz, 2H), 8.3 (d, J = 7.2 Hz, 2H), 8.1-8.0 (m, 2H), 7.91-7.81 (m, 7H), 7.6-7.4 (m, 11H), 7.38-7.22 (m, 7H), 1.67 (s, 12H). | 991.31 | 991.21 |
| 142 | δ = 9.03 (s, 1H), 8.8 (d, J = 7.2 Hz, 2H), 8.1-8.0 (m, 4H), 7.91 (d, J = 7.5 Hz, 1H), 7.81-7.7 (m, 6H), 7.54-7.4 (m, 5H), 7.35-7.3 (m, 9H). | 807.19 | 806.93 |

TABLE 2-continued

| Compound No. | $^1$H NMR (CDCl$_3$, 300 MHz) | MS/FAB found | MS/FAB calculated |
|---|---|---|---|
| 143 | δ = 9.03 (s, 1H), 8.4 (d, J = 7.2 Hz, 2H), 8.1-8.0 (m, 2H), 7.91-7.81 (m, 5H), 7.7-7.5 (m, 7H), 7.45-7.32 (m, 7H), 6.6 (s, 2H), 1.71 (s, 6H). | 787.22 | 786.94 |
| 144 | δ = 9.28 (s, 1H), 8.4 (d, J = 7.2 Hz, 2H), 8.15-8.0 (m, 2H), 7.90-7.84 (m, 3H), 7.7-7.5 (m, 6H), 7.4-7.32 (m, 5H), 6.6 (s, 2H), 2.55 (s, 3H), 1.71 (s, 6H). | 725.20 | 724.87 |
| 145 | δ = 9.28 (s, 1H), 8.4 (d, J = 7.2 Hz, 2H), 8.15-8.0 (m, 2H), 7.90-7.84 (m, 3H), 7.7-7.5 (m, 6H), 7.4-7.32 (m, 5H), 6.6 (s, 2H), 2.7 (m, 1H), 1.71 (s, 6H), 1.23 (d, J = 2.2 Hz, 6H). | 753.23 | 752.92 |
| 146 | δ = 9.03 (s, 1H), 8.4 (d, J = 7.2 Hz, 2H), 8.01-7.9 (m, 5H), 7.81-7.6 (m, 6H), 7.54-7.4 (m, 7H), 7.3-7.28 (m, 2H), 6.6 (s, 2H), 1.71 (s, 6H), 1.34 (s, 9H). | 843.28 | 843.05 |
| 147 | δ = 9.0 (s, 1H), 8.1 (d, J = 7.2 Hz, 2H), 8.01-7.9 (m, 5H), 7.84-7.8 (m, 4H), 7.7 (d, J = 7.2 Hz, 2H), 7.6-7.54 (m, 5H), 7.45-7.4 (m, 5H), 7.3-7.1 (m, 6H), 1.41 (s, 9H). | 915.28 | 915.00 |
| 148 | δ = 9.01 (s, 1H), 8.1 (d, J = 7.2 Hz, 2H), 8.01-7.9 (m, 7H) 7.8-7.75 (m, 6H), 7.6-7.4 (m, 11H), 7.3-7.2 (m, 12H), 1.35 (s, 9H) | 1067.34 | 1067.00 |
| 149 | δ = 9.03 (s, 1H), 8.1 (d, J = 8.1 Hz, 2H), 8.01 (d, J = 7.6 Hz, 1H), 8 (d, J = 7.5 Hz, 2H), 7.91-7.81 (m, 6H), 7.7 (d, J = 8.1 Hz, 2H), 7.6-7.4 (m, 13H), 7.3-7.2 (m, 12H), 1.34 (s, 9H). | 1067.34 | 1067.00 |
| 150 | δ = 9.02 (s, 1H), 8.1 (d, J = 7.2 Hz, 2H), 8.01 (d, J = 7.0 Hz, 1H), 7.91-7.8 (m, 6H), 7.7-7.65 (m, 4H), 7.6-7.4 (m, 11H), 7.3 (m, 2H), 7.0 (m, 2H), 1.38 (s, 9H). | 951.26 | 951.09 |
| 151 | δ = 9.03 (s, 1H), 8.1 (d, J = 8.1 Hz, 2H), 8.01 (d, J = 7.6 Hz, 1H), 7.91-7.86 (m, 4H), 7.81-7.77 (m, 6H), 7.7 (s, 1H), 7.6-7.4 (m, 11H), 7.4-7.3 (m, 10H), 7.0 (d, J = 5.6 Hz, 2H), 1.34 (s, 9H). | 1103.32 | 1103.28 |
| 152 | δ = 9.03 (s, 1H), 8.1-7.9 (m, 9H), 7.81 (d, J = 7.5 Hz, 2H), 7.7 (d, J = 7.1 Hz, 2H), 7.6-7.4 (m, 13H), 7.3-7.22 (m, 12H), 1.34 (s, 9H). | 1103.32 | 1103.28 |
| 153 | δ = 9.03 (s, 1H), 8.5 (d, J = 7.7 Hz, 2H), 8.01-7.81 (m, 7H), 7.7 (d, J = 7.1 Hz, 2H), 7.6-7.4 (m, 9H), 7.3 (d, J = 8.0 Hz, 4H), 7.26-7.23 (m, 6H), 7.2 (s, 2H), 7.14 (m, 2H), 1.34 (s, 9H). | 967.31 | 967.19 |
| 154 | δ = 9.03 (m, 1H), 8.1-7.81 (m, 9H), 7.7-7.6 (m, 4H), 7.54-7.4 (m, 9H), 7.3-7.14 (m, 12H), 1.34 (s, 9H) | 967.31 | 967.19 |
| 155 | δ = 9.03 (s, 1H), 8.56 (d, J = 2.8 Hz, 2H), 8.1-8.0 (m, 3H), 7.95-7.9 (m, 2H), 7.81 (d, J = 7.6 Hz, 2H), 7.54-7.45 (m, 9H), 7.3-6.98 (m, 8H), 1.34 (s, 9H). | 815.25 | 814.99 |
| 156 | δ = 9.0 (s, 1H), 8.5 (d, J = 7.2 Hz, 2H), 8.01-7.9 (m, 7H), 7.81 (d, J = 7.5 Hz, 2H), 7.7 (d, J = 7.2 Hz, 2H), 7.6-7.5 (m, 5H), 7.45-7.4 (m, 4H), 7.3-7.1 (m, 8H), 1.34 (s, 9H). | 915.28 | 915.11 |
| 157 | δ = 9.03 (s, 1H), 8.56 (d, J = 6.2 Hz, 2H), 8.3 (s, 2H), 8.01 (d, J = 7.3 Hz, 1H), 7.9-7.81 (m, 8H), 7.6-7.46 (m, 9H). 7.4-7.3 (m, 6H), 6.9-6.7 (m, 2H), 1.67 (s, 12H), 1.34 (s, 9H). | 1047.37 | 1047.31 |

EXAMPLE 1

Manufacture of an OLED

An OLED device was manufactured by using a red phosphorescent compound according to the invention.

First, a transparent electrode ITO thin film (15 Ω/□) (2) obtained from a glass for OLED (produced by Samsung Corning) was subjected to ultrasonic washing with trichloroethylene, acetone, ethanol and distilled water, sequentially, and stored in isopronanol before use.

Then, an ITO substrate was equipped in a substrate folder of a vacuum vapor-deposit device, and 4,4',4''-tris(N,N-(2-naphthyl)-phenylamino)triphenylamine (2-TNATA) was placed in a cell of the vacuum vapor-deposit device, which was then ventilated up to $10^{-6}$ torr of vacuum in the chamber. Electric current was applied to the cell to evaporate 2-TNATA, thereby providing vapor-deposit of a hole injection layer (3) having 60 nm of thickness on the ITO substrate.

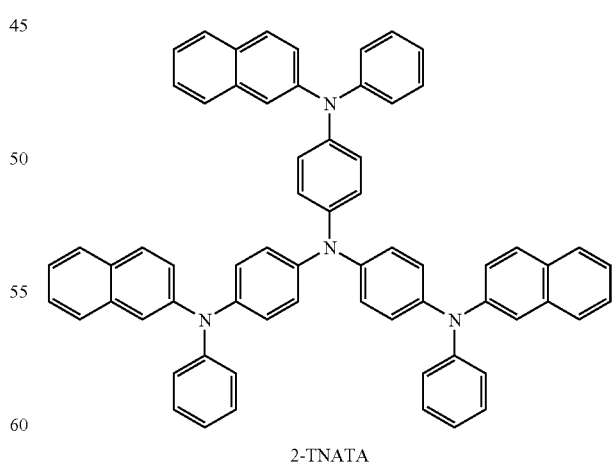

2-TNATA

Then, to another cell of the vacuum vapor-deposit device, charged was N,N'-bis(α-naphthyl)-N,N'-diphenyl-4,4'-diamine (NPB), and electric current was applied to the cell to evaporate NPB, thereby providing vapor-deposit of a hole transportation layer (4) of 20 nm of thickness on the hole injection layer.

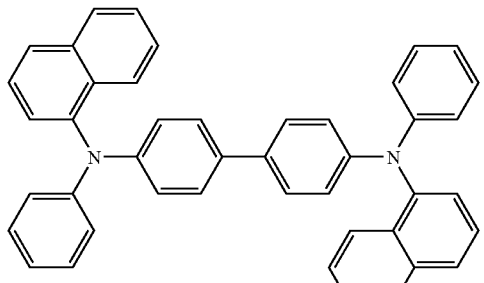

NPB

In another cell of said vacuum vapor-deposit device, charged was 4,4'-N,N'-dicarbazole-biphenyl (CBP) as an electroluminescent host material, and a red phosphorescent compound according to the present invention was charged to still another cell. The two materials were evaporated at different rates to carry out doping to vapor-deposit an electroluminescent layer (5) having 30 nm of thickness on the hole transportation layer. The suitable doping concentration is 4 to 10 mol % on the basis of CBP.

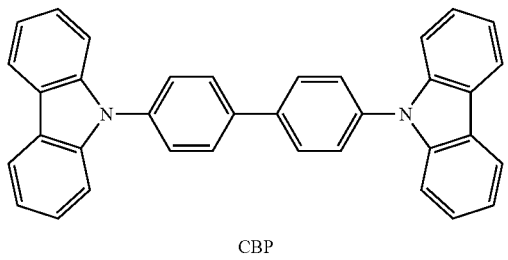

CBP

Then, on the electroluminescent layer, bis(2-methyl-8-quinolinato)(p-phenylphenolato)aluminum (III) (BAlq) was vapor-deposited as a hole blocking layer in a thickness of 10 nm, tris(8-hydroxyquinoline)aluminum (III) (Alq) was vapor-deposited as an electron transportation layer (6) in a thickness of 20 nm, and then lithium quinolate (Liq) was vapor-deposited as an electron injection layer (7) in a thickness of 1 to 2 nm. Thereafter, an Al cathode (8) was vapor-deposited in a thickness of 150 nm by using another vacuum vapor-deposit device to manufacture an OLED.

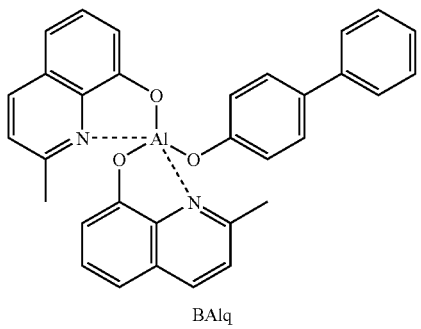

BAlq

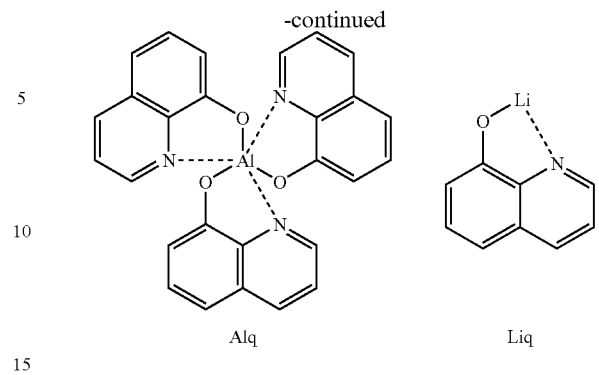

Alq · · · Liq

EXAMPLE 2

Evaluation of Optical Properties of Electroluminescent Materials

The complexes having high synthetic yield were purified by vacuum sublimation at $10^{-6}$ torr and used as a dopant for an electroluminescent layer of an OLED, but in case of the material having low synthetic yield, photoluminescence peaks were simply confirmed. The photoluminescence peaks were measured by preparing a solution in methylene chloride with a concentration or $10^{-4}$ M or less. In every measurement of photoluminescence of each material, the wavelength of excitation was 250 nm.

In order to confirm the performance of the OLED's prepared according to Example 1, the luminous efficiency of the OLED's was measured at 10 mA/cm². Various properties are shown in Tables 3 and 4.

TABLE 3

| Material | n | L' | Structure of L' | Color coordinate (x, y) | EL (nm) | Max. luminous efficiency (cd/A) |
|---|---|---|---|---|---|---|
| 101 | 2 | 1 | Acac | (0.64, 0.36) | 616 | 8.78 |
| 102 | 2 | 1 | Acac | (0.64, 0.36) | 612 | 10.3 |
| 103 | 2 | 1 | Acac | (0.63, 0.36) | 614 | 8.95 |
| 104 | 2 | 1 | Acac | (0.65, 0.35) | 618 | 8.80 |
| 105 | 2 | 1 | Acac | (0.66, 0.33) | 630 | 4.92 |
| 106 | 2 | 1 | Acac | (0.60, 0.40) | 598 | 15.5 |
| 107 | 2 | 1 | Acac | (0.66, 0.34) | 626 | 4.98 |
| 108 | 2 | 1 | Acac | (0.66, 0.34) | 620 | 8.54 |
| 109 | 2 | 1 | Acac | (0.61, 0.39) | 604 | 13.3 |
| 110 | 2 | 1 | Acac | (0.65, 0.35) | 618 | 8.59 |
| 111 | 2 | 1 | Acac | (0.63, 0.36) | 612 | 6.87 |
| 112 | 2 | 1 | Acac | (0.63, 0.36) | 614 | 4.56 |
| 113 | 2 | 1 | Acac | (0.65, 0.34) | 622 | 5.92 |
| 114 | 2 | 1 | Acac | (0.64, 0.36) | 616 | 7.72 |
| 115 | 2 | 1 | Acac | (0.65, 0.35) | 620 | 7.23 |
| 116 | 2 | 1 | Acac | (0.63, 0.37) | 610 | 12.2 |
| 117 | 2 | 1 | Acac | (0.63, 0.36) | 614 | 7.58 |
| 118 | 2 | 1 | Acac | (0.66, 0.34) | 626 | 3.3 |
| 119 | 2 | 1 | Acac | (0.69, 0.31) | 640 | 2.06 |
| 120 | 2 | 1 | Acac | (0.70, 0.30) | 642 | 1.5 |
| 121 | 2 | 1 | Acac | (0.64, 0.35) | 622 | 4.4 |
| 122 | 2 | 1 | Acac | (0.67, 0.32) | 626 | 2.63 |
| 123 | 2 | 1 | Acac | (0.68, 0.30) | 634 | 2.18 |
| 124 | 2 | 1 | Acac | (0.66, 0.32) | 628 | 3.56 |
| 125 | 2 | 1 | Acac | (0.63, 0.35) | 618 | 6.28 |
| 126 | 2 | 1 | Acac | (0.64, 0.35) | 620 | 3.4 |
| 127 | 2 | 1 | Acac | (0.61, 0.28) | 612 | 5.8 |
| 128 | 2 | 1 | Acac | (0.67, 0.34) | 624 | 4.3 |
| 129 | 2 | 1 | Acac | (0.63, 0.36) | 614 | 5.5 |
| 130 | 2 | 1 | Acac | (0.68, 0.32) | 622 | 3.8 |

TABLE 3-continued

| Material | n | L' | Structure of L' | Color coordinate (x, y) | EL (nm) | Max. luminous efficiency (cd/A) |
|---|---|---|---|---|---|---|
| 131 | 2 | 1 | Acac | (0.66, 0.34) | 620 | 6.8 |
| 132 | 2 | 1 | Acac | (0.64, 0.36) | 616 | 8.1 |

Table 3 shows device properties of the electroluminescent materials developed according to the present invention, wherein n=2 and L'=1, and particularly the L' is comprised of only subsidiary ligands of acac type, in the general structure of the material developed by the present invention.

The synthesized material (101), having phenyl for $R_1$ and hydrogen for $R_2$, $R_3$, $R_4$, $R_7$, $R_8$, $R_9$ and $R_{10}$ shows excellent properties: 616 nm of wavelength, color coordinate (0.64, 0.36), and 8.78 cd/A of luminous efficiency.

The electroluminescent materials (102, 104, 105, 107 and 108), having alkyl group or aromatic ring introduced at $R_7$, $R_8$ or $R_9$, showed wavelength change of 2~14 nm, as compared to material (101). The electroluminescent material (102), though having the shift toward shorter wavelength by about 4 nm, showed narrow width of the EL peak without change in color coordinate, and increased luminous efficiency. The electroluminescent materials (113~116) wherein an aromatic ring has been introduced at $R_1$, showed somewhat different shift of wavelength depending on the binding position. The electroluminescent material (116), with shift toward shorter wavelength by 6 nm as compared to that of material (101), exhibited the color coordinate (0.63, 0.37).

TABLE 4

| Material | n | L' | Structure of L' | Color coordinate (x, y) | EL (nm) | Max. luminous efficiency (cd/A) |
|---|---|---|---|---|---|---|
| 133 | 2 | 1 | Pq | (0.65, 0.35) | 616 | 6.83 |
| 134 | 2 | 1 | Ppy | (0.65, 0.35) | 620 | 5.83 |
| 135 | 2 | 1 | Piq | (0.65, 0.34) | 620 | 5.36 |
| 136 | 2 | 1 | Pyfl | (0.65, 0.35) | 620 | 5.52 |
| 137 | 2 | 1 | Bq | (0.65, 0.34) | 618 | 6.10 |
| 138 | 1 | 2 | Pq | (0.64, 0.36) | 612 | 9.7 |
| 139 | 1 | 2 | Ppy | (0.66, 0.34) | 628 | 4.76 |
| 140 | 1 | 2 | Piq | (0.67, 0.33) | 624 | 8.50 |
| 141 | 1 | 2 | Pyfl | (0.64, 0.36) | 616 | 7.01 |
| 142 | 1 | 2 | Bq | (0.64, 0.36) | 614 | 7.75 |
| 143 | 1 | 2 | Priq | (0.64, 0.36) | 608 | 6.7 |
| 144 | 1 | 2 | Priq | (0.66, 0.34) | 610 | 6.24 |
| 145 | 1 | 2 | Priq | (0.66, 0.34) | 610 | 6.57 |
| 146 | 1 | 2 | Priq | (0.65, 0.35) | 608 | 6.66 |
| 147 | 1 | 2 | Pq | (0.64, 0.36) | 616 | 7.93 |
| 148 | 1 | 2 | 2,6-Dpq | (0.62, 0.37) | 610 | 5.40 |
| 149 | 1 | 2 | Dpq | (0.65, 0.35) | 622 | 12.5 |
| 150 | 1 | 2 | PqF | (0.64, 0.36) | 608 | 15.6 |
| 151 | 1 | 2 | 2,6-DpqF | (0.64, 0.36) | 614 | 6.48 |
| 152 | 1 | 2 | 2,4-DpqF | (0.65, 0.35) | 618 | — |
| 153 | 1 | 2 | Peiq | (0.70, 0.30) | 648 | 2.51 |
| 154 | 1 | 2 | Peq | (0.68, 0.31) | 626 | 3.46 |
| 155 | 1 | 2 | Ppy | (0.65, 0.35) | 612 | 6.83 |
| 156 | 1 | 2 | Piq | (0.68, 0.32) | 620 | 8.8 |
| 157 | 1 | 2 | Pyfl | (0.66, 0.34) | 610 | 6.48 |

Table 4 shows device properties of phosphorescent materials consisting of primary ligands and subsidiary ligands having alkyl or aromatic ring substituted at $R_1$ or $R_9$ of the material developed according to the present invention. It is recognized that the electroluminescent materials have various range of EL wavelength depending upon the type of primary or subsidiary ligand(s).

When the materials developed according to the invention are used as a subsidiary ligand of various luminous body (n=1), color coordinate and efficiency, and in particular, chemical stability of the primary luminous body can be enhanced. Material (140) using piq luminous body, and the material developed according to the invention as a subsidiary ligand, provides the device with good properties: 624 nm of electroluminescent wavelength, color coordinate (0.67, 0.33), and 8.5 cd/A of luminous efficiency. Particularly, the color coordinate corresponds to deep red range satisfying that of NTSC. Ir(piq)$_3$ has more or less unstable bonding with slightly distorted binding of ligands to Ir core metal. Structural stability was enhanced by using the material developed according to the invention as a subsidiary ligand instead of three Piq ligands.

FIG. 1 is a cross-sectional view of an OLED; and FIGS. 2 to 5 show EL spectrum, current density-voltage property, luminance-voltage property and luminous efficiency-luminance property of an OLED employing the red phosphorescent compound (102) according to the present invention as a dopant.

It is also found that current property is improved even in conventional CBP:dopant/HBL, when a red phosphorescent compound according to the invention is employed as a dopant.

The red electroluminescent compounds according to the present invention, being a compound of more beneficial skeletal in terms of better properties than conventional red phosphorescent materials, show more excellent EL properties. Thus, the results of advancement in developing OLED's of medium to large size are anticipated if the red electroluminescent compounds according to the present invention are applied to OLED panels.

What is claimed is:

1. An organic phosphorescent compound represented by Chemical Formula (1):

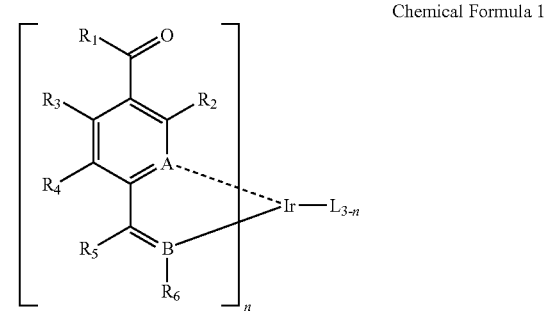

Chemical Formula 1 wherein, L is an organic ligand;

A is N; B is C;

$R_1$ represents $(C_6-C_{20})$aryl;

$R_2$ through $R_4$ independently represent hydrogen, linear or branched $(C_1-C_{20})$alkyl, $(C_1-C_{20})$alkoxy, $(C_3-C_{12})$cycloalkyl, $(C_6-C_{20})$aryl, halogen, tri$(C_1-C_{20})$alkylsilyl or tri$(C_6-C_{20})$arylsilyl;

$R_5$ and $R_6$ independently represent hydrogen, a linear or branched $(C_1-C_{20})$alkyl, $(C_6-C_{20})$aryl or halogen; $R_5$ and $R_6$ may be linked via $(C_3-C_{12})$alkylene or $(C_3-C_{12})$alkenylene with or without a fused ring to form an alicyclic ring, or a monocyclic or polycyclic aromatic ring;

the alkyl or aryl of $R_5$ and $R_6$, or the alicyclic ring, or the monocyclic or polycyclic aromatic ring formed therefrom by linkage via $(C_3-C_{12})$alkylene or $(C_3-C_{12})$alkenylene with or without a fused ring may be further substituted by one or more substituent(s) selected from linear or branched $(C_1-C_{20})$alkyl optionally substituted with halogen, $(C_1-C_{20})$alkoxy, halogen, tri$(C_1-C_{20})$alkylsilyl, tri$(C_6-C_{20})$arylsilyl and $(C_6-C_{20})$aryl;

the aryl of $R_1$ and the alkyl, alkoxy, cycloalkyl and aryl of $R_2$ through $R_4$ may be further substituted by one or more substituent(s) selected from linear or branched $(C_1-C_{20})$ alkyl optionally substituted with halogen, $(C_1-C_{20})$ alkoxy, halogen, tri$(C_1-C_{20})$alkylsilyl, tri$(C_6-C_{20})$arylsilyl and $(C_6-C_{20})$aryl; and n is an integer from 1 to 3.

2. An organic phosphorescent compound according to claim 1, wherein the alicyclic ring, or the monocyclic or polycyclic aromatic ring formed from $R_5$ and $R_6$ by linkage via $(C_3-C_{12})$alkylene or $(C_3-C_{12})$alkenylene with or without a fused ring is benzene, naphthalene, anthracene, fluorene, indene, phenanthrene or pyridine.

3. An organic phosphorescent compound according to claim 1, which is selected from the group consisting of the compounds represented by one of Chemical Formulas (2) to (6):

Chemical Formula 2

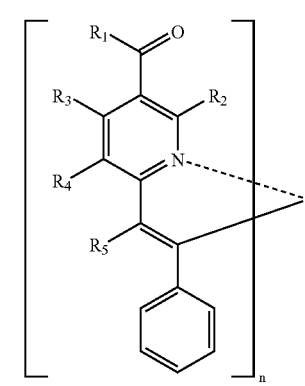

Chemical Formula 3

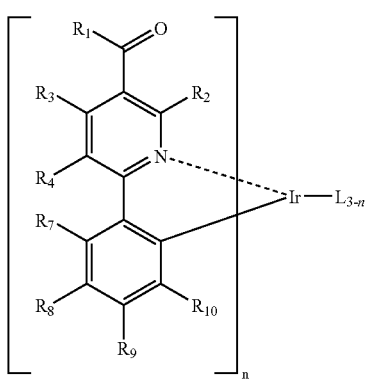

Chemical Formula 4

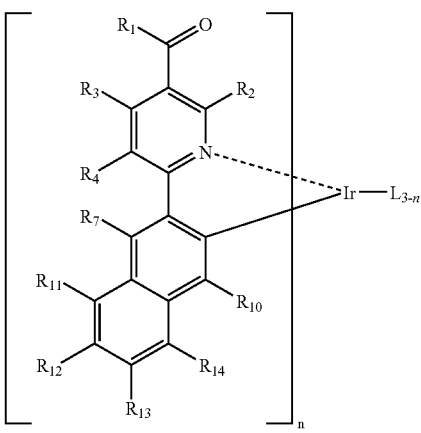

Chemical Formula 5

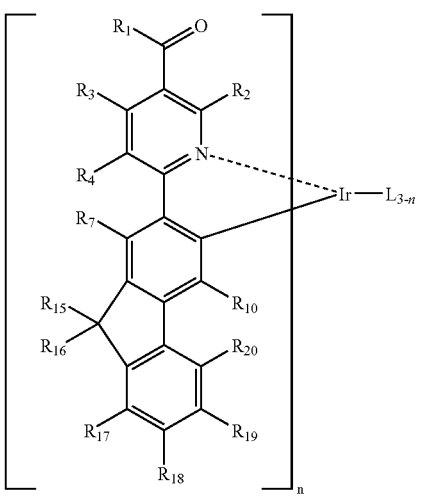

Chemical Formula 6

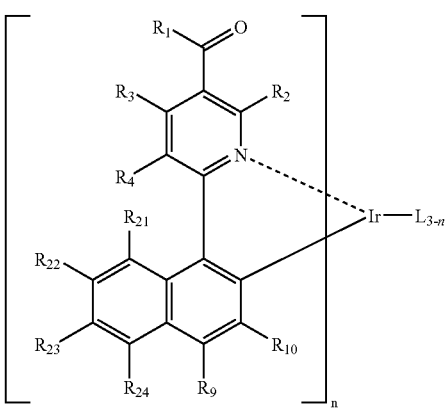

wherein, L, $R_1$, $R_2$, $R_3$, $R_4$, $R_5$ and n are defined as in claim 1;

$R_7$ through $R_{14}$ and $R_{17}$ through $R_{24}$ independently represent hydrogen, linear or branched $(C_1-C_{20})$alkyl optionally substituted with halogen, $(C_1-C_{20})$alkoxy, halogen, tri$(C_1-C_{20})$alkylsilyl, tri$(C_6-C_{20})$arylsilyl or $(C_6-C_{20})$ aryl; and $R_{15}$ and $R_{16}$ independently represent hydrogen or linear or branched $(C_1-C_{20})$alkyl.

4. An organic phosphorescent compound according to claim 3, which is selected from the group consisting of compounds represented by one of the following chemical formulas:
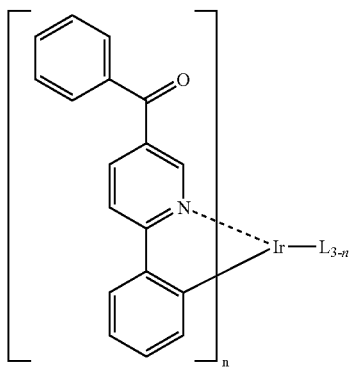
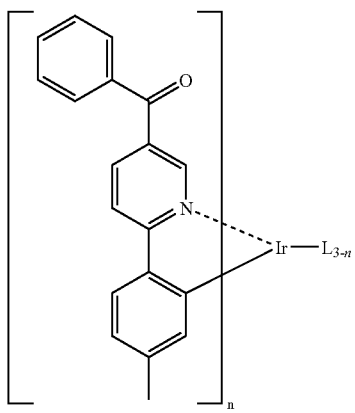
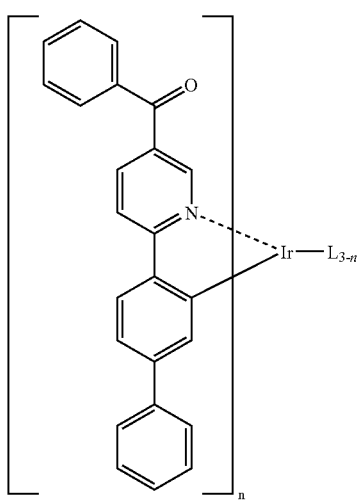
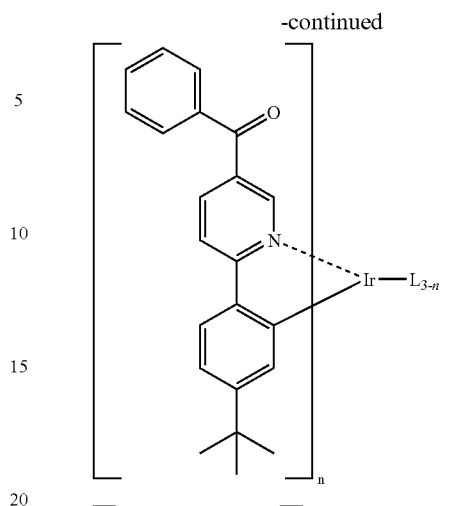
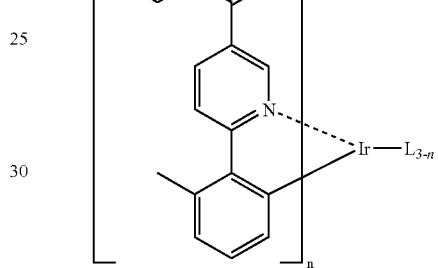
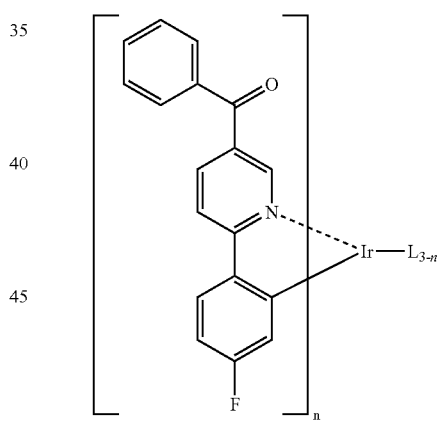
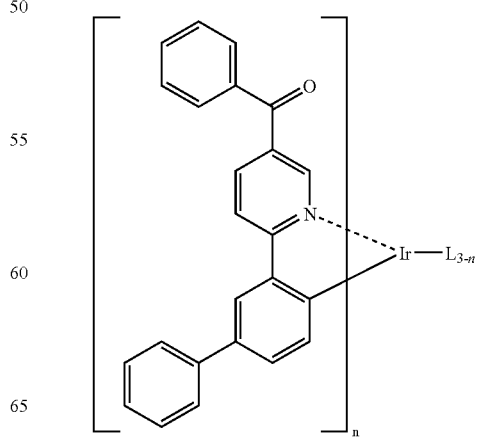

-continued
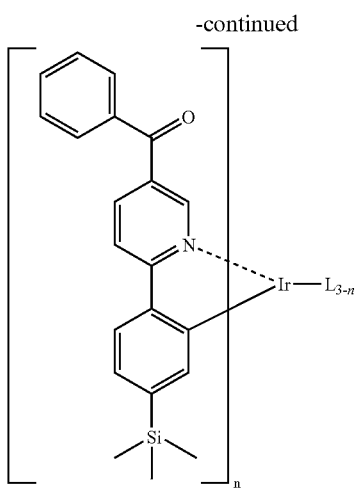
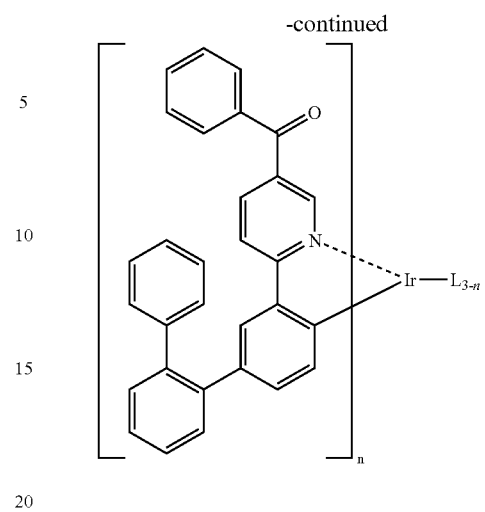
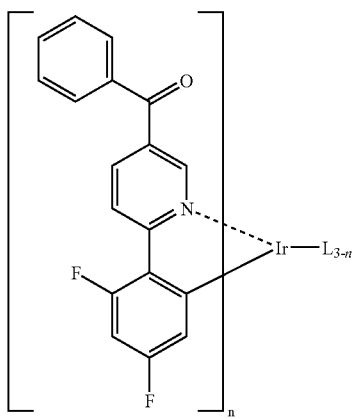
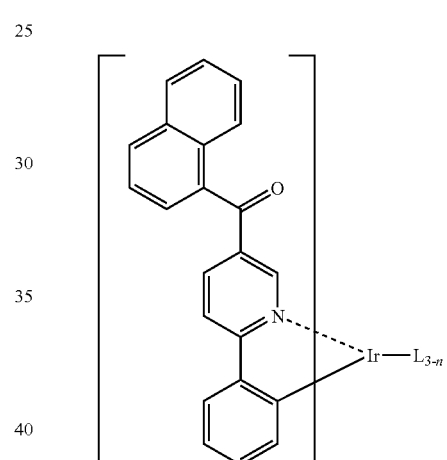
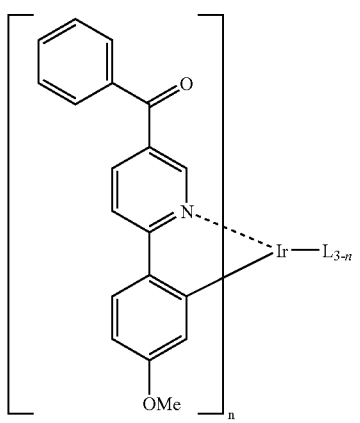
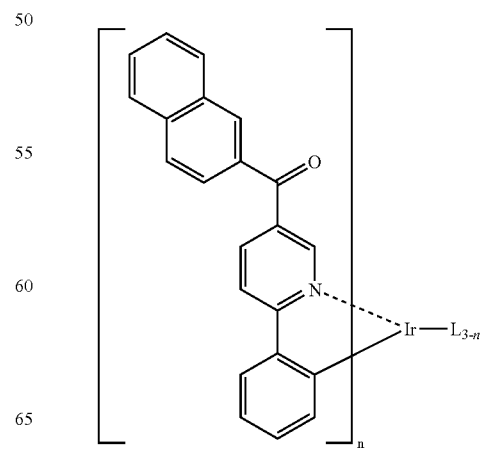

-continued
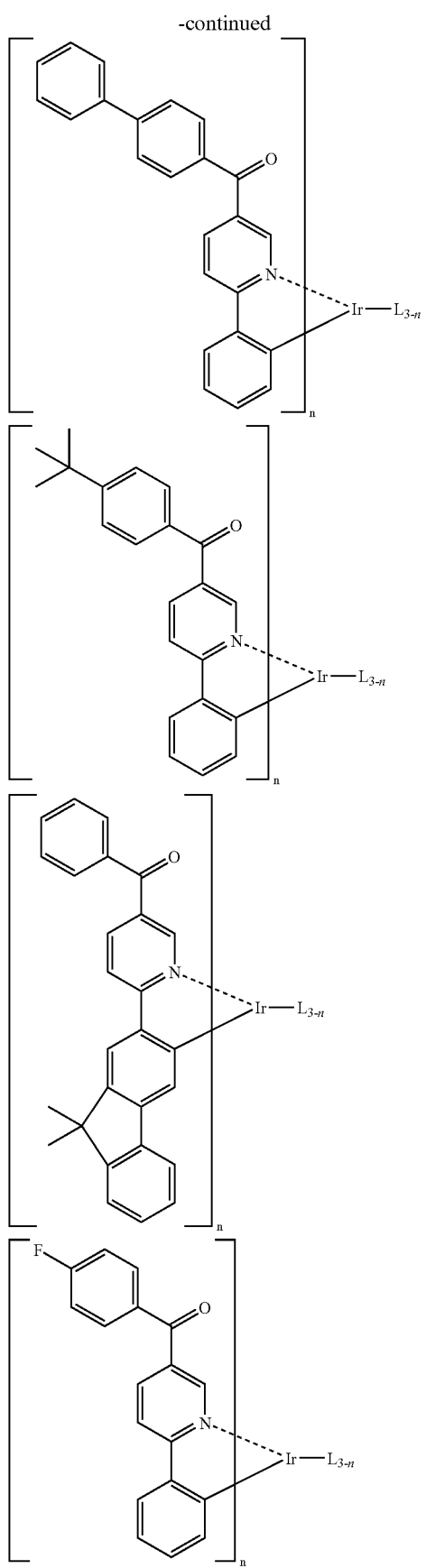
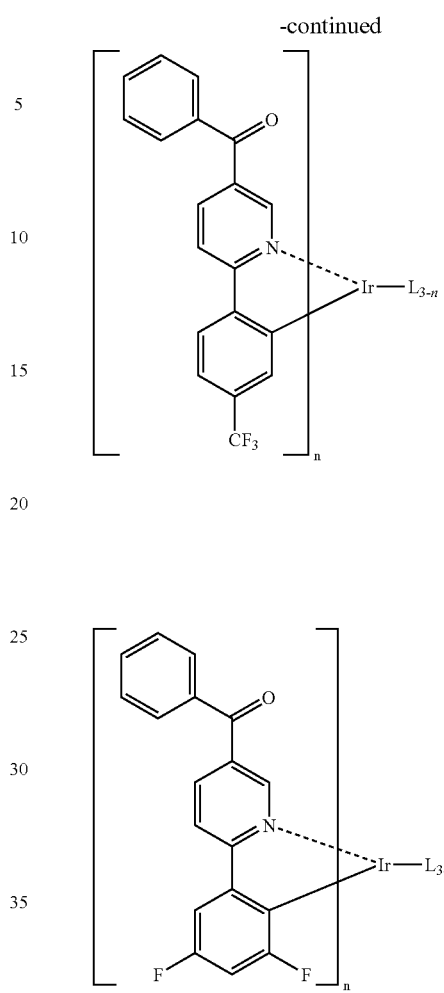
wherein, L is an organic ligand, and n is an integer from 1 to 3.
5. An organic phosphorescent compound according to claim 4, wherein the ligand (L) has a structure represented by one of the following chemical formulas:
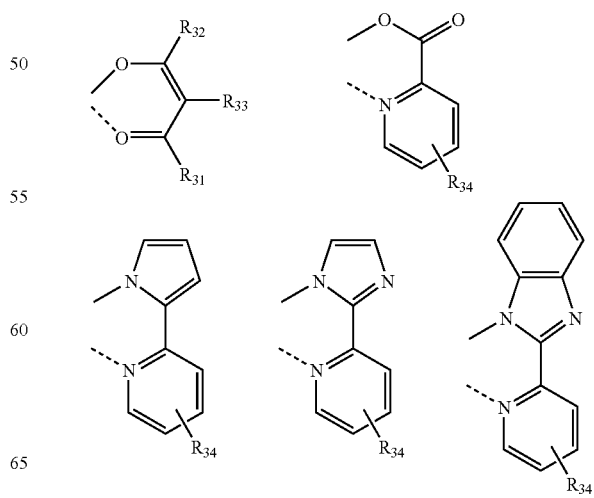

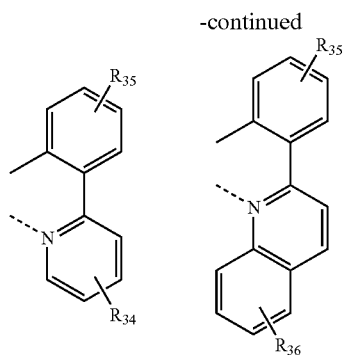
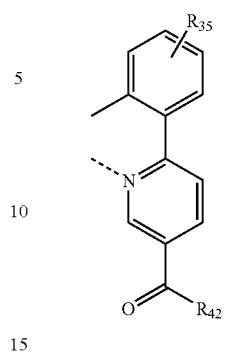
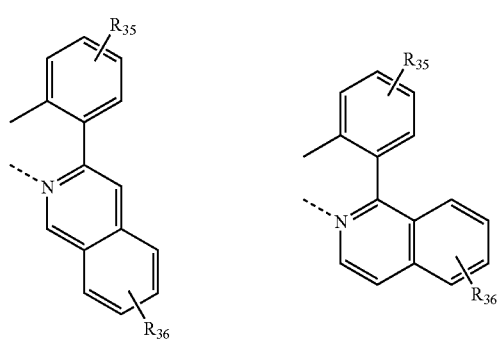
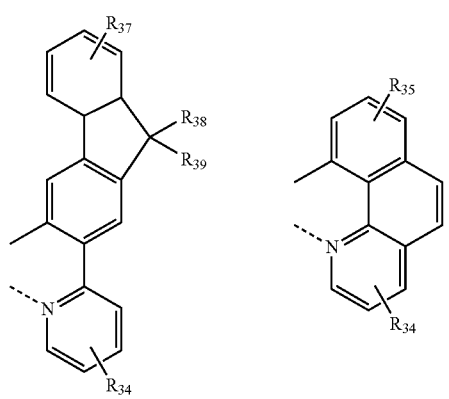
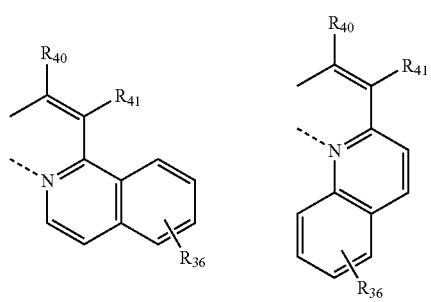

wherein, $R_{31}$ and $R_{32}$ independently represent hydrogen, a linear or branched $(C_1-C_{20})$alkyl optionally substituted with halogen, phenyl optionally substituted with linear or branched $(C_1-C_{20})$alkyl, or halogen;

$R_{33}$ through $R_{37}$ independently represent hydrogen, linear or branched $(C_1-C_{20})$alkyl, phenyl optionally substituted with linear or branched $(C_1-C_{20})$alkyl, tri$(C_1-C_{20})$alkylsilyl or halogen;

$R_{38}$ through $R_{41}$ independently represent hydrogen, linear or branched $(C_1-C_{20})$alkyl, phenyl optionally substituted with linear or branched $(C_1-C_{20})$alkyl; and $R_{42}$ represents a linear or branched $(C_1-C_{20})$alkyl, phenyl optionally substituted with linear or branched $(C_1-C_{20})$alkyl, or halogen.

6. An organic phosphorescent compound according to claim 5, wherein the ligand (L) has a structure represented by one of the following chemical formulas:

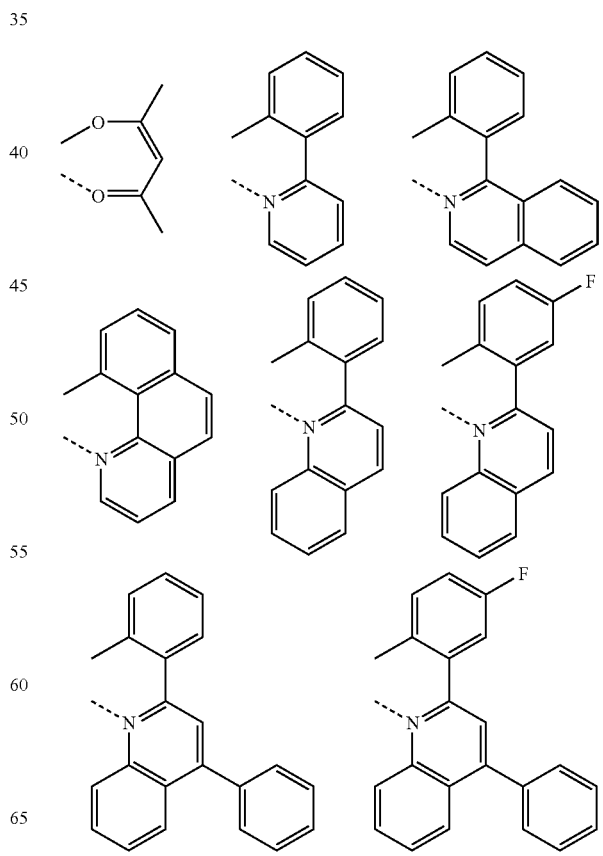

-continued

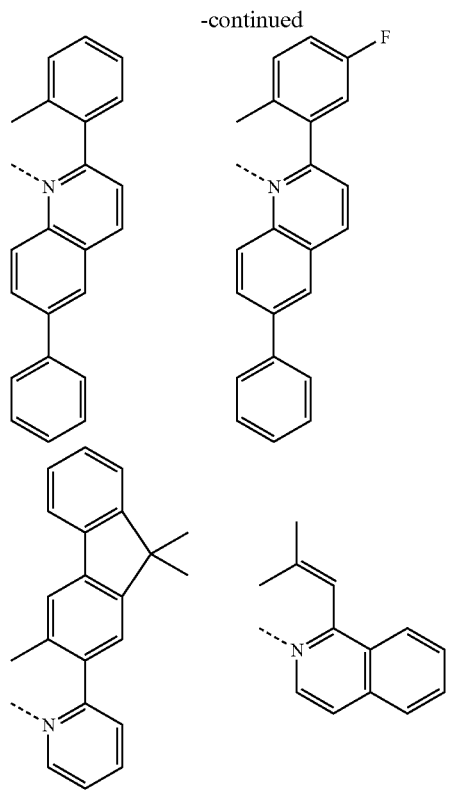

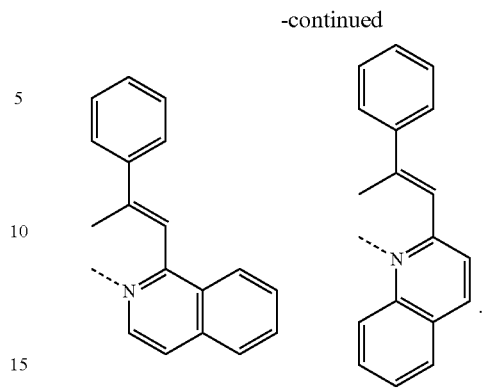

7. An organic phosphorescent compound according to claim 3, wherein $R_1$ represents, phenyl, biphenyl, naphthyl, t-butylphenyl or fluorophenyl; $R_2$ through $R_5$ independently represent hydrogen, methyl, ethyl, n-propyl, i-propyl, n-butyl or t-butyl; $R_7$ through $R_{14}$ and $R_{17}$ through $R_{24}$ independently represent hydrogen, methyl, ethyl, n-propyl, i-propyl, n-butyl, t-butyl, fluoro, methoxy, ethoxy, butoxy, phenyl, biphenyl, trimethylsilyl, triphenylsilyl or trifluoromethyl; and $R_{15}$ and $R_{16}$ independently represent hydrogen or methyl.

8. An organic electroluminescent device comprising an organic phosphorescent compound according to claim 1.

* * * * *